United States Patent
Pacheco-Serrant et al.

(10) Patent No.: US 11,471,145 B2
(45) Date of Patent: Oct. 18, 2022

(54) ARTICULATED INSTRUMENTATION AND METHODS OF USING THE SAME

(71) Applicant: Spinal Elements, Inc., Carlsbad, CA (US)

(72) Inventors: Helson Pacheco-Serrant, El Paso, TX (US); Justin Taber, Honolulu, HI (US); Douglas M. Lorang, San Jose, CA (US); Laurent B. Schaller, Los Altos, CA (US); Patricia McHale, Mountain View, CA (US); Michael Baldwin, San Jose, CA (US); Richard G. Fessler, Winnetka, IL (US); Joshua M. Ammerman, Bethesda, MA (US)

(73) Assignee: Spinal Elements, Inc., Carlsbad, CA (US)

( * ) Notice: Subject to any disclaimer, the term of this patent is extended or adjusted under 35 U.S.C. 154(b) by 0 days.

(21) Appl. No.: 17/023,312

(22) Filed: Sep. 16, 2020

(65) Prior Publication Data

US 2021/0169459 A1 Jun. 10, 2021

Related U.S. Application Data

(63) Continuation of application No. PCT/US2019/022632, filed on Mar. 15, 2019.

(60) Provisional application No. 62/644,101, filed on Mar. 16, 2018.

(51) Int. Cl.
*A61B 17/02* (2006.01)
*A61F 2/44* (2006.01)
*A61F 2/46* (2006.01)

(52) U.S. Cl.
CPC .......... *A61B 17/025* (2013.01); *A61F 2/4455* (2013.01); *A61F 2/4611* (2013.01); *A61B 2017/0256* (2013.01); *A61F 2002/4635* (2013.01)

(58) Field of Classification Search
CPC ............ A61B 17/1613; A61B 17/1624; A61B 17/1631; A61B 17/1633; A61B 17/1659; A61B 17/1671; A61B 17/32002; A61B 2017/320032
See application file for complete search history.

(56) References Cited

U.S. PATENT DOCUMENTS

| | | | |
|---|---|---|---|
| 2,002,021 | A | 5/1935 | Rouse |
| 3,807,390 | A | 4/1974 | Ostrowski et al. |
| 4,846,175 | A | 7/1989 | Frimberger |

(Continued)

FOREIGN PATENT DOCUMENTS

| | | |
|---|---|---|
| DE | 42 22 121 | 9/1993 |
| DE | 197 10 392 | 7/1999 |

(Continued)

OTHER PUBLICATIONS

Official Communication in European Application No. 08730402.8, dated Feb. 18, 2013.

(Continued)

*Primary Examiner* — Eduardo C Robert
*Assistant Examiner* — Steven J Cotroneo
(74) *Attorney, Agent, or Firm* — Knobbe, Martens, Olson & Bear, LLP

(57) ABSTRACT

Articulated instruments that include tools for disrupting and/or distracting tissue, and methods of using the same.

20 Claims, 29 Drawing Sheets

(56) References Cited

U.S. PATENT DOCUMENTS

| | | |
|---|---|---|
| 4,862,891 A | 9/1989 | Smith |
| 4,863,476 A | 9/1989 | Shepperd |
| 4,898,161 A | 2/1990 | Grundei |
| 5,129,889 A | 7/1992 | Hahn et al. |
| 5,192,327 A | 3/1993 | Brantigan |
| 5,201,742 A | 4/1993 | Hasson |
| 5,219,358 A | 6/1993 | Bendel et al. |
| 5,267,994 A | 12/1993 | Gentelia et al. |
| 5,306,310 A | 4/1994 | Siebels |
| 5,342,394 A | 8/1994 | Matsuno et al. |
| 5,345,945 A | 9/1994 | Hodgson et al. |
| 5,366,490 A | 11/1994 | Edwards et al. |
| 5,374,267 A | 12/1994 | Siegal |
| 5,383,884 A | 1/1995 | Summers |
| 5,397,304 A | 3/1995 | Truckai |
| 5,397,364 A | 3/1995 | Kozak et al. |
| 5,423,806 A | 6/1995 | Dale et al. |
| 5,433,739 A | 7/1995 | Sluijter et al. |
| 5,445,639 A | 8/1995 | Kuslich et al. |
| 5,470,043 A | 11/1995 | Marts et al. |
| 5,487,757 A | 1/1996 | Truckai et al. |
| 5,500,012 A | 3/1996 | Brucker et al. |
| 5,540,696 A | 7/1996 | Booth, Jr. et al. |
| 5,549,679 A | 8/1996 | Kuslich |
| 5,554,163 A | 9/1996 | Shturman |
| 5,571,147 A | 11/1996 | Sluijter et al. |
| 5,571,189 A | 11/1996 | Kuslich |
| 5,599,346 A | 2/1997 | Edwards et al. |
| 5,697,909 A | 12/1997 | Eggers et al. |
| 5,716,416 A | 2/1998 | Lin |
| 5,718,707 A | 2/1998 | Mikhail |
| 5,755,661 A | 5/1998 | Schwartzman |
| 5,755,732 A | 5/1998 | Green et al. |
| 5,755,797 A | 5/1998 | Baumgartner |
| 5,788,713 A | 8/1998 | Dubach et al. |
| 5,851,214 A | 12/1998 | Larsen et al. |
| 5,871,501 A | 2/1999 | Leschinsky et al. |
| 5,885,217 A | 3/1999 | Gisselberg et al. |
| 5,916,166 A | 6/1999 | Reiss et al. |
| 5,919,235 A | 7/1999 | Husson et al. |
| 5,980,471 A | 11/1999 | Jafari |
| 5,980,504 A | 11/1999 | Sharkey et al. |
| 6,007,570 A | 12/1999 | Sharkey et al. |
| 6,019,765 A | 2/2000 | Thornhill et al. |
| 6,039,761 A | 3/2000 | Li et al. |
| 6,059,829 A | 5/2000 | Schläpfer et al. |
| 6,099,514 A | 8/2000 | Sharkey et al. |
| 6,126,660 A | 10/2000 | Dietz |
| 6,126,682 A | 10/2000 | Sharkey et al. |
| 6,183,517 B1 | 2/2001 | Suddaby |
| 6,224,630 B1 | 5/2001 | Bao et al. |
| 6,228,022 B1 | 5/2001 | Friesem et al. |
| 6,245,072 B1 | 6/2001 | Zdeblick |
| 6,245,107 B1 | 6/2001 | Ferree |
| 6,277,112 B1 | 8/2001 | Underwood et al. |
| 6,332,895 B1 | 12/2001 | Suddaby |
| 6,375,635 B1 | 4/2002 | Moutafis et al. |
| 6,387,130 B1 | 5/2002 | Stone et al. |
| 6,419,704 B1 | 7/2002 | Ferree |
| 6,436,142 B1 | 8/2002 | Paes et al. |
| 6,454,806 B1 | 9/2002 | Cohen et al. |
| 6,468,270 B1 | 10/2002 | Hovda et al. |
| 6,488,710 B2 | 12/2002 | Besselink |
| 6,491,690 B1 | 12/2002 | Goble et al. |
| 6,500,205 B1 | 12/2002 | Michelson |
| 6,530,926 B1 | 3/2003 | Davison |
| 6,551,319 B2 | 4/2003 | Lieberman |
| 6,554,833 B2 | 4/2003 | Levy et al. |
| 6,558,383 B2 | 5/2003 | Cunningham et al. |
| 6,558,386 B1 | 5/2003 | Cragg |
| 6,558,390 B2 | 5/2003 | Cragg |
| 6,562,033 B2 | 5/2003 | Shah et al. |
| 6,592,625 B2 | 7/2003 | Cauthen |
| 6,595,998 B2 | 7/2003 | Johnson et al. |
| 6,602,248 B1 | 8/2003 | Sharps et al. |
| 6,607,505 B1 | 8/2003 | Thompson et al. |
| 6,607,530 B1 | 8/2003 | Carl et al. |
| 6,620,196 B1 | 9/2003 | Trieu |
| 6,656,178 B1 | 12/2003 | Veldhuizen et al. |
| 6,670,505 B1 | 12/2003 | Collins et al. |
| 6,676,665 B2 | 1/2004 | Foley et al. |
| 6,714,822 B2 | 3/2004 | King et al. |
| 6,726,684 B1 | 4/2004 | Woloszko et al. |
| 6,733,496 B2 | 5/2004 | Sharkey et al. |
| 6,749,605 B2 | 6/2004 | Ashley et al. |
| 6,764,491 B2 | 7/2004 | Frey et al. |
| 6,767,347 B2 | 7/2004 | Sharkey et al. |
| 6,773,432 B1 | 8/2004 | Clayman et al. |
| 6,821,276 B2 | 11/2004 | Lambrecht et al. |
| 6,830,570 B1 | 12/2004 | Frey et al. |
| 6,878,155 B2 | 4/2005 | Sharkey et al. |
| 6,923,811 B1 | 8/2005 | Carl et al. |
| 6,939,351 B2 | 9/2005 | Eckman |
| 6,953,458 B2 | 10/2005 | Loeb |
| 6,964,667 B2 | 11/2005 | Shaolian et al. |
| 6,976,949 B2 | 12/2005 | Winkler et al. |
| 7,004,970 B2 | 2/2006 | Cauthen III et al. |
| 7,008,432 B2 | 3/2006 | Schlapfer et al. |
| 7,025,765 B2 | 4/2006 | Balbierz et al. |
| 7,052,516 B2 | 5/2006 | Cauthen, III et al. |
| 7,056,321 B2 | 6/2006 | Pagliuca et al. |
| 7,069,087 B2 | 6/2006 | Sharkey et al. |
| 7,087,055 B2 | 8/2006 | Lim et al. |
| 7,087,058 B2 | 8/2006 | Cragg |
| 7,114,501 B2 | 10/2006 | Johnson et al. |
| 7,124,761 B2 | 10/2006 | Lambrecht et al. |
| 7,144,397 B2 | 12/2006 | Lambrecht et al. |
| 7,179,225 B2 | 2/2007 | Shluzas et al. |
| 7,204,853 B2 | 4/2007 | Gordon et al. |
| 7,211,055 B2 | 5/2007 | Diederich et al. |
| 7,241,297 B2 | 7/2007 | Shaolian et al. |
| 7,252,686 B2 | 8/2007 | Garrison et al. |
| 7,267,687 B2 | 9/2007 | McGuckin, Jr. |
| 7,282,020 B2 | 10/2007 | Kaplan |
| 7,309,336 B2 | 12/2007 | Ashley et al. |
| 7,318,823 B2 | 1/2008 | Sharps et al. |
| 7,318,826 B2 | 1/2008 | Teitelbaum et al. |
| 7,322,962 B2 | 1/2008 | Forrest |
| 7,331,956 B2 | 2/2008 | Hovda et al. |
| 7,331,963 B2 | 2/2008 | Bryan et al. |
| RE40,156 E | 3/2008 | Sharps et al. |
| 7,618,458 B2 | 11/2009 | Biedermann et al. |
| 7,682,378 B2 | 3/2010 | Truckai et al. |
| 7,753,912 B2 | 7/2010 | Raymond et al. |
| 7,758,647 B2 | 7/2010 | Arnin et al. |
| 7,771,432 B2 | 8/2010 | Schwab et al. |
| 7,776,051 B2 | 8/2010 | Colleran et al. |
| 7,824,445 B2 | 11/2010 | Biro et al. |
| 7,887,568 B2 | 2/2011 | Ahlgren |
| 7,901,460 B2 | 3/2011 | Sherman |
| 7,922,767 B2 | 4/2011 | Sack et al. |
| 7,947,078 B2 | 5/2011 | Siegal |
| 7,963,915 B2 | 6/2011 | Bleich |
| 8,021,429 B2 | 9/2011 | Viker |
| 8,025,697 B2 | 9/2011 | McClellan, III et al. |
| 8,083,796 B1 | 12/2011 | Raiszadeh et al. |
| 8,123,750 B2 | 2/2012 | Norton et al. |
| 8,128,662 B2 | 3/2012 | Altarac et al. |
| 8,137,401 B2 | 3/2012 | Stad et al. |
| 8,142,507 B2 | 3/2012 | McGuckin, Jr. |
| 8,246,622 B2 | 8/2012 | Siegal et al. |
| 8,252,001 B2 | 8/2012 | Quimo et al. |
| 8,252,054 B2 | 8/2012 | Greenhalgh et al. |
| 8,377,070 B2 | 2/2013 | Gauthier |
| 8,394,102 B2 | 3/2013 | Garabedian et al. |
| 8,454,617 B2 | 6/2013 | Schaller et al. |
| 8,454,622 B2 | 6/2013 | Blain et al. |
| 8,470,043 B2 | 6/2013 | Schaller et al. |
| 8,579,980 B2 | 11/2013 | DeLurio et al. |
| 8,628,577 B1 | 1/2014 | Jimenez |
| 8,632,591 B2 | 1/2014 | Vila et al. |
| 8,663,332 B1 | 3/2014 | To et al. |
| 8,685,031 B2 | 4/2014 | Kleiner et al. |
| 8,764,806 B2 | 7/2014 | Abdou |

(56) References Cited

U.S. PATENT DOCUMENTS

| | | |
|---|---|---|
| 8,906,028 B2 | 12/2014 | Kleiner |
| 8,968,408 B2 | 3/2015 | Schaller et al. |
| 8,974,464 B2 | 3/2015 | Johnson et al. |
| 8,979,860 B2 | 3/2015 | Voellmicke et al. |
| 8,986,385 B2 | 3/2015 | Hall |
| 9,034,041 B2 | 5/2015 | Wolters et al. |
| 9,039,771 B2 | 5/2015 | Glerum et al. |
| 9,161,773 B2 | 10/2015 | Schaller et al. |
| 9,308,022 B2 | 4/2016 | Chitre et al. |
| 9,351,851 B2 | 5/2016 | Huffmaster et al. |
| 9,480,574 B2 | 11/2016 | Lee et al. |
| 9,566,170 B2 | 2/2017 | Schell et al. |
| 9,642,712 B2 | 5/2017 | Schaller et al. |
| 9,827,031 B2 | 11/2017 | Emery et al. |
| 9,955,961 B2 | 5/2018 | Huffmaster et al. |
| 10,022,243 B2 | 7/2018 | Emery et al. |
| 10,231,843 B2 | 3/2019 | Lee et al. |
| 10,258,228 B2 | 4/2019 | Genovese et al. |
| 10,285,821 B2 | 5/2019 | Schaller et al. |
| 10,314,605 B2 | 6/2019 | Huffmaster et al. |
| 10,426,629 B2 | 10/2019 | Schaller et al. |
| 10,575,963 B2 | 3/2020 | Schaller et al. |
| 10,709,577 B2 | 7/2020 | Lorang et al. |
| 10,758,286 B2 | 9/2020 | Ammerman et al. |
| 11,224,453 B2 | 1/2022 | Huffmaster et al. |
| 2001/0023348 A1 | 9/2001 | Ashley et al. |
| 2001/0029377 A1 | 10/2001 | Aebi et al. |
| 2001/0031981 A1 | 10/2001 | Evans et al. |
| 2002/0019637 A1 | 2/2002 | Frey et al. |
| 2002/0026197 A1 | 2/2002 | Foley et al. |
| 2002/0128716 A1 | 9/2002 | Cohen et al. |
| 2002/0147444 A1 | 10/2002 | Shah et al. |
| 2002/0156530 A1 | 10/2002 | Lambrecht et al. |
| 2003/0009223 A1 | 1/2003 | Fehling et al. |
| 2003/0014047 A1 | 1/2003 | Woloszko et al. |
| 2003/0040796 A1 | 2/2003 | Ferree |
| 2003/0065358 A1 | 4/2003 | Frecker et al. |
| 2003/0083747 A1 | 5/2003 | Winterbottom et al. |
| 2003/0158545 A1 | 8/2003 | Hovda et al. |
| 2003/0158553 A1 | 8/2003 | Michelson |
| 2003/0187453 A1 | 10/2003 | Schlapfer et al. |
| 2003/0204189 A1 | 10/2003 | Cragg |
| 2003/0220650 A1 | 11/2003 | Major et al. |
| 2004/0002762 A1 | 1/2004 | Hawkins |
| 2004/0015218 A1 | 1/2004 | Finch et al. |
| 2004/0024463 A1 | 2/2004 | Thomas, Jr. et al. |
| 2004/0049180 A1 | 3/2004 | Sharps et al. |
| 2004/0059333 A1 | 3/2004 | Carl et al. |
| 2004/0064144 A1 | 4/2004 | Johnson et al. |
| 2004/0073216 A1 | 4/2004 | Lieberman |
| 2004/0087994 A1 | 5/2004 | Suddaby |
| 2004/0092988 A1 | 5/2004 | Shaolian et al. |
| 2004/0102774 A1 | 5/2004 | Trieu |
| 2004/0106940 A1 | 6/2004 | Shaolian et al. |
| 2004/0116922 A1 | 6/2004 | Hovda et al. |
| 2004/0127893 A1 | 7/2004 | Hovda |
| 2004/0148028 A1 | 7/2004 | Ferree et al. |
| 2004/0153064 A1 | 8/2004 | Foley et al. |
| 2004/0167625 A1 | 8/2004 | Beyar et al. |
| 2004/0193158 A1 | 9/2004 | Lim et al. |
| 2004/0230198 A1 | 11/2004 | Manzi et al. |
| 2004/0230309 A1 | 11/2004 | DiMauro et al. |
| 2004/0249464 A1 | 12/2004 | Bindseil et al. |
| 2004/0260305 A1 | 12/2004 | Gorensek et al. |
| 2005/0021030 A1 | 1/2005 | Pagliuca et al. |
| 2005/0021041 A1 | 1/2005 | Michelson |
| 2005/0033292 A1 | 2/2005 | Teitelbaum et al. |
| 2005/0038517 A1 | 2/2005 | Carrison et al. |
| 2005/0049623 A1 | 3/2005 | Moore et al. |
| 2005/0065610 A1 | 3/2005 | Pisharodi |
| 2005/0070911 A1 | 3/2005 | Carrison et al. |
| 2005/0080425 A1 | 4/2005 | Bhatnagar et al. |
| 2005/0090833 A1 | 4/2005 | DiPoto |
| 2005/0090899 A1 | 4/2005 | DiPoto |
| 2005/0107878 A1 | 5/2005 | Conchy |
| 2005/0113832 A1 | 5/2005 | Molz, IV et al. |
| 2005/0119750 A1 | 6/2005 | Studer |
| 2005/0131540 A1 | 6/2005 | Trieu |
| 2005/0131541 A1 | 6/2005 | Trieu |
| 2005/0137601 A1 | 6/2005 | Assell et al. |
| 2005/0137605 A1 | 6/2005 | Assell et al. |
| 2005/0149049 A1 | 7/2005 | Assell et al. |
| 2005/0165420 A1* | 7/2005 | Cha ............... A61B 17/1671 606/150 |
| 2005/0182414 A1 | 8/2005 | Manzi et al. |
| 2005/0182416 A1 | 8/2005 | Lim et al. |
| 2005/0187537 A1 | 8/2005 | Loeb et al. |
| 2005/0203527 A1 | 9/2005 | Carrison et al. |
| 2005/0228391 A1 | 10/2005 | Levy et al. |
| 2005/0234493 A1 | 10/2005 | Carr et al. |
| 2005/0240171 A1 | 10/2005 | Forrest |
| 2005/0251134 A1 | 11/2005 | Woloszko et al. |
| 2005/0251177 A1 | 11/2005 | Saadat et al. |
| 2005/0256525 A1 | 11/2005 | Culbert et al. |
| 2005/0261683 A1 | 11/2005 | Veldhuizen et al. |
| 2005/0261684 A1 | 11/2005 | Shaolian et al. |
| 2005/0261692 A1 | 11/2005 | Carrison et al. |
| 2005/0273173 A1 | 12/2005 | Gordon et al. |
| 2005/0278027 A1 | 12/2005 | Hyde |
| 2006/0015131 A1 | 1/2006 | Kierce et al. |
| 2006/0025797 A1 | 2/2006 | Lock et al. |
| 2006/0030933 A1 | 2/2006 | DeLegge et al. |
| 2006/0036241 A1 | 2/2006 | Siegal |
| 2006/0041258 A1 | 2/2006 | Galea |
| 2006/0041295 A1 | 2/2006 | Osypka |
| 2006/0047178 A1 | 3/2006 | Winkler et al. |
| 2006/0052793 A1 | 3/2006 | Heinz |
| 2006/0058826 A1 | 3/2006 | Evans et al. |
| 2006/0058876 A1 | 3/2006 | McKinley |
| 2006/0074425 A1 | 4/2006 | Sutterlin et al. |
| 2006/0089646 A1 | 4/2006 | Bonutti |
| 2006/0116689 A1 | 6/2006 | Albans |
| 2006/0129244 A1 | 6/2006 | Ensign et al. |
| 2006/0136064 A1 | 6/2006 | Sherman |
| 2006/0149268 A1 | 7/2006 | Truckai et al. |
| 2006/0161162 A1 | 7/2006 | Lambrecht et al. |
| 2006/0178666 A1 | 8/2006 | Cosman et al. |
| 2006/0189999 A1 | 8/2006 | Zwirkoski |
| 2006/0195091 A1 | 8/2006 | McGraw et al. |
| 2006/0195094 A1 | 8/2006 | McGraw et al. |
| 2006/0206116 A1 | 9/2006 | Yeung |
| 2006/0217811 A1 | 9/2006 | Lambrecht et al. |
| 2006/0224154 A1 | 10/2006 | Shadduck et al. |
| 2006/0224241 A1 | 10/2006 | Butler et al. |
| 2006/0229625 A1 | 10/2006 | Truckai et al. |
| 2006/0235418 A1 | 10/2006 | Gil et al. |
| 2006/0241577 A1 | 10/2006 | Balbierz et al. |
| 2006/0247600 A1 | 11/2006 | Yeung et al. |
| 2006/0247784 A1 | 11/2006 | Kim |
| 2006/0265076 A1 | 11/2006 | Carter et al. |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0010848 A1 | 1/2007 | Leung et al. |
| 2007/0016273 A1 | 1/2007 | Scarborough et al. |
| 2007/0027545 A1 | 2/2007 | Carls et al. |
| 2007/0050030 A1 | 3/2007 | Kim |
| 2007/0055259 A1 | 3/2007 | Norton et al. |
| 2007/0055262 A1 | 3/2007 | Tomita et al. |
| 2007/0060935 A1 | 3/2007 | Schwardt et al. |
| 2007/0067035 A1 | 3/2007 | Falahee |
| 2007/0093822 A1 | 4/2007 | Dutoit et al. |
| 2007/0093899 A1 | 4/2007 | Dutoit et al. |
| 2007/0118219 A1 | 5/2007 | Hyde, Jr. |
| 2007/0123888 A1 | 5/2007 | Bleich et al. |
| 2007/0123903 A1 | 5/2007 | Raymond et al. |
| 2007/0123986 A1 | 5/2007 | Schaller et al. |
| 2007/0149978 A1 | 6/2007 | Shezifi et al. |
| 2007/0149990 A1 | 6/2007 | Palmer et al. |
| 2007/0162032 A1 | 7/2007 | Johnson et al. |
| 2007/0162062 A1 | 7/2007 | Norton et al. |
| 2007/0162127 A1 | 7/2007 | Peterman et al. |
| 2007/0162135 A1 | 7/2007 | Segal et al. |

(56) References Cited

U.S. PATENT DOCUMENTS

| | | |
|---|---|---|
| 2007/0168041 A1 | 7/2007 | Kadiyala |
| 2007/0168043 A1 | 7/2007 | Ferree |
| 2007/0173939 A1 | 7/2007 | Kim et al. |
| 2007/0175959 A1 | 8/2007 | Shelton, IV et al. |
| 2007/0198021 A1 | 8/2007 | Wales |
| 2007/0198025 A1 | 8/2007 | Trieu et al. |
| 2007/0208426 A1 | 9/2007 | Trieu |
| 2007/0213704 A1 | 9/2007 | Truckai et al. |
| 2007/0213733 A1 | 9/2007 | Bleich et al. |
| 2007/0213734 A1 | 9/2007 | Bleich et al. |
| 2007/0213735 A1 | 9/2007 | Saadat et al. |
| 2007/0225703 A1 | 9/2007 | Schmitz et al. |
| 2007/0233143 A1 | 10/2007 | Josse et al. |
| 2007/0255286 A1 | 11/2007 | Trieu |
| 2007/0255406 A1 | 11/2007 | Trieu |
| 2007/0255703 A1 | 11/2007 | Maruyama et al. |
| 2007/0260252 A1 | 11/2007 | Schmitz et al. |
| 2007/0260270 A1 | 11/2007 | Assell et al. |
| 2007/0260315 A1 | 11/2007 | Foley et al. |
| 2007/0265652 A1 | 11/2007 | Assell et al. |
| 2007/0265691 A1 | 11/2007 | Swanson |
| 2007/0276406 A1 | 11/2007 | Mahoney et al. |
| 2007/0299521 A1 | 12/2007 | Glenn et al. |
| 2008/0009826 A1 | 1/2008 | Miller et al. |
| 2008/0009828 A1 | 1/2008 | Miller et al. |
| 2008/0009847 A1 | 1/2008 | Ricart et al. |
| 2008/0009875 A1 | 1/2008 | Sankaran et al. |
| 2008/0009876 A1 | 1/2008 | Sankaran et al. |
| 2008/0009877 A1 | 1/2008 | Sankaran et al. |
| 2008/0015639 A1 | 1/2008 | Bjork et al. |
| 2008/0021435 A1 | 1/2008 | Miller et al. |
| 2008/0027407 A1 | 1/2008 | Miller et al. |
| 2008/0033465 A1 | 2/2008 | Schmitz et al. |
| 2008/0058707 A1 | 3/2008 | Ashley et al. |
| 2008/0065080 A1 | 3/2008 | Assell et al. |
| 2008/0065092 A1 | 3/2008 | Assell et al. |
| 2008/0065093 A1 | 3/2008 | Assell et al. |
| 2008/0065094 A1 | 3/2008 | Assell et al. |
| 2008/0086157 A1 | 4/2008 | Stad et al. |
| 2008/0114367 A1 | 5/2008 | Meyer |
| 2008/0147113 A1 | 6/2008 | Nobis et al. |
| 2008/0161809 A1* | 7/2008 | Schmitz ............ A61B 17/1659 606/79 |
| 2008/0177259 A1 | 7/2008 | Wu |
| 2008/0183204 A1 | 7/2008 | Greenhalgh et al. |
| 2008/0221687 A1 | 9/2008 | Viker |
| 2008/0228135 A1 | 9/2008 | Snoderly |
| 2008/0249628 A1 | 10/2008 | Altarac et al. |
| 2008/0287995 A1 | 11/2008 | Gauthier |
| 2008/0294171 A1 | 11/2008 | Boehm, Jr. et al. |
| 2008/0300636 A1 | 12/2008 | Carli et al. |
| 2009/0012612 A1 | 1/2009 | White et al. |
| 2009/0024217 A1 | 1/2009 | Levy et al. |
| 2009/0105711 A1 | 4/2009 | Mitchell et al. |
| 2009/0143716 A1 | 6/2009 | Lowry et al. |
| 2009/0157187 A1 | 6/2009 | Richelsoph |
| 2009/0198241 A1 | 8/2009 | Phan |
| 2009/0198245 A1 | 8/2009 | Phan |
| 2009/0234454 A1 | 9/2009 | Siegal |
| 2010/0030216 A1 | 2/2010 | Arcenio |
| 2010/0114179 A1 | 5/2010 | Moore et al. |
| 2010/0131005 A1 | 5/2010 | Conlon |
| 2010/0179578 A1* | 7/2010 | Tannoury ............ A61B 17/32 606/170 |
| 2010/0185291 A1 | 7/2010 | Jimenez et al. |
| 2010/0198263 A1 | 8/2010 | Siegal et al. |
| 2010/0228091 A1 | 9/2010 | Widenhouse et al. |
| 2010/0249798 A1* | 9/2010 | Sournac ............ A61B 17/7076 606/104 |
| 2010/0262147 A1 | 10/2010 | Siegal et al. |
| 2010/0262242 A1 | 10/2010 | Chavatte et al. |
| 2010/0268234 A1* | 10/2010 | Aho ............ A61B 17/1617 606/80 |
| 2010/0286782 A1 | 11/2010 | Schaller et al. |
| 2010/0298864 A1 | 11/2010 | Castro |
| 2011/0015638 A1 | 1/2011 | Pischl et al. |
| 2011/0015747 A1 | 1/2011 | McManus et al. |
| 2011/0112455 A1 | 5/2011 | Rocklin |
| 2011/0125266 A1 | 5/2011 | Rodgers et al. |
| 2011/0144440 A1 | 6/2011 | Cropper et al. |
| 2011/0172722 A1 | 7/2011 | Verhulst et al. |
| 2011/0208306 A1 | 8/2011 | Farris |
| 2011/0245926 A1 | 10/2011 | Kitchen |
| 2011/0307063 A1 | 12/2011 | Schaller et al. |
| 2012/0022651 A1 | 1/2012 | Akyuz et al. |
| 2012/0071977 A1 | 3/2012 | Oglaza et al. |
| 2012/0071980 A1 | 3/2012 | Purcell et al. |
| 2012/0089231 A1 | 4/2012 | Prestigiacomo |
| 2012/0123426 A1 | 5/2012 | Quimo |
| 2012/0136442 A1 | 5/2012 | Kleiner |
| 2012/0136448 A1 | 5/2012 | Seifert et al. |
| 2012/0150241 A1 | 6/2012 | Ragab et al. |
| 2012/0232664 A1 | 9/2012 | Ulrich et al. |
| 2012/0277861 A1 | 11/2012 | Steele et al. |
| 2012/0283748 A1 | 11/2012 | Ortiz et al. |
| 2012/0296171 A1* | 11/2012 | Lovell ............ A61B 17/0218 600/213 |
| 2013/0053863 A1 | 2/2013 | Juravic et al. |
| 2013/0110239 A1 | 5/2013 | Siegal et al. |
| 2013/0116791 A1 | 5/2013 | Theofilos |
| 2013/0144391 A1 | 6/2013 | Siegal et al. |
| 2013/0158667 A1 | 6/2013 | Tabor et al. |
| 2013/0204374 A1 | 8/2013 | Milella, Jr. |
| 2013/0238098 A1 | 9/2013 | Schaller et al. |
| 2013/0282143 A1 | 10/2013 | Perkins et al. |
| 2013/0304070 A1* | 11/2013 | Nelson ............ A61B 17/1659 606/85 |
| 2014/0058513 A1 | 2/2014 | Gahman et al. |
| 2014/0067073 A1 | 3/2014 | Hauck |
| 2014/0163326 A1 | 6/2014 | Forsell |
| 2014/0163560 A1* | 6/2014 | Fenn ............ A61B 17/1659 606/84 |
| 2014/0235949 A1 | 8/2014 | Smith |
| 2014/0236296 A1 | 8/2014 | Wagner et al. |
| 2014/0249629 A1 | 9/2014 | Moskowitz et al. |
| 2014/0257484 A1 | 9/2014 | Flower et al. |
| 2014/0277481 A1 | 9/2014 | Lee et al. |
| 2014/0316427 A1 | 10/2014 | Yoon et al. |
| 2015/0012000 A1* | 1/2015 | Siegal ............ A61B 17/1671 606/80 |
| 2015/0051701 A1 | 2/2015 | Glerum et al. |
| 2015/0100124 A1 | 4/2015 | Whipple |
| 2015/0112437 A1 | 4/2015 | Davis et al. |
| 2015/0112438 A1 | 4/2015 | McLean |
| 2015/0148908 A1 | 5/2015 | Marino et al. |
| 2015/0367487 A1* | 12/2015 | Nino ............ A61B 17/1624 81/473 |
| 2016/0007979 A1 | 1/2016 | Bhagat et al. |
| 2016/0287409 A1* | 10/2016 | Ziemek ............ A61F 2/4611 |
| 2016/0367332 A1 | 12/2016 | Shah et al. |
| 2017/0135704 A1 | 5/2017 | Abbasi |
| 2017/0303938 A1* | 10/2017 | Rindal ............ A61B 17/8625 |
| 2019/0167440 A1 | 6/2019 | Lee et al. |
| 2019/0216482 A1 | 7/2019 | Huffmaster et al. |
| 2019/0216612 A1 | 7/2019 | Schaller et al. |
| 2020/0345401 A1 | 11/2020 | McHale et al. |
| 2021/0113252 A1 | 4/2021 | Ammerman et al. |
| 2021/0154024 A1 | 5/2021 | Lorang et al. |
| 2022/0031471 A1 | 2/2022 | Hessler et al. |

FOREIGN PATENT DOCUMENTS

| | | |
|---|---|---|
| EP | 0 682 910 | 11/1995 |
| EP | 1 157 676 | 11/2001 |
| FR | 2 900 814 | 11/2007 |
| JP | 2002-028171 | 1/2002 |
| WO | WO 98/017190 | 4/1998 |
| WO | WO 98/034552 | 8/1998 |
| WO | WO 99/021500 | 5/1999 |
| WO | WO 99/047058 | 9/1999 |
| WO | WO 00/074605 | 12/2000 |
| WO | WO 03/024344 | 3/2003 |
| WO | WO 2005/048856 | 6/2005 |

(56) References Cited

FOREIGN PATENT DOCUMENTS

| WO | WO 2006/047587 | 5/2006 |
|---|---|---|
| WO | WO 2006/072941 | 7/2006 |
| WO | WO 2007/100914 | 9/2007 |
| WO | WO 2008/036505 | 3/2008 |
| WO | WO 2008/084479 | 7/2008 |
| WO | WO 2008/103832 | 8/2008 |
| WO | WO 2010/008353 | 1/2010 |
| WO | WO 2011/150350 | 12/2011 |
| WO | WO 2012/048187 | 4/2012 |
| WO | WO 2012/178018 | 12/2012 |
| WO | WO 2013/043850 | 3/2013 |
| WO | WO 2014/158680 | 10/2014 |
| WO | WO 2019/148083 | 8/2019 |
| WO | WO 2019/178575 | 9/2019 |

OTHER PUBLICATIONS

International Search Report and Written Opinion in International Application No. PCT/US2008/054590, dated Aug. 22, 2008.
International Preliminary Report on Patentability and Written Opinion in International Application No. PCT/US2008/054590, dated Aug. 28, 2009.
International Search Report and Written Opinion in International Application No. PCT/US2019/015386, dated May 23, 2019.
International Preliminary Report on Patentability and Written Opinion in International Application No. PCT/US2019/015386, dated Aug. 13, 2020.
International Search Report and Written Opinion in International Application No. PCT/US2019/022632, dated May 30, 2019.
International Preliminary Report on Patentability and Written Opinion in International Application No. PCT/US2019/022632, dated Oct. 1, 2020.
International Search Report and Written Opinion in International Application No. PCT/US2014/019246, dated Aug. 19, 2014.
International Preliminary Report on Patentability and Written Opinion in International Application No. PCT/US2014/019246, dated Sep. 24, 2015.
Office Communication for U.S. Appl. No. 13/804,847, dated Jul. 13, 2015.
Office Communication for U.S. Appl. No. 13/804,847, dated Oct. 16, 2015.
Extended European Search Report for European Patent Application No. 11787510.4, dated Oct. 15, 2013.
International Search Report and Written Opinion for PCT Patent Application No. PCT/US2011/038377, dated Aug. 25, 2011.
International Search Report and Written Opinion for PCT Patent Application No. PCT/US2013/068906, dated Feb. 6, 2014.

* cited by examiner

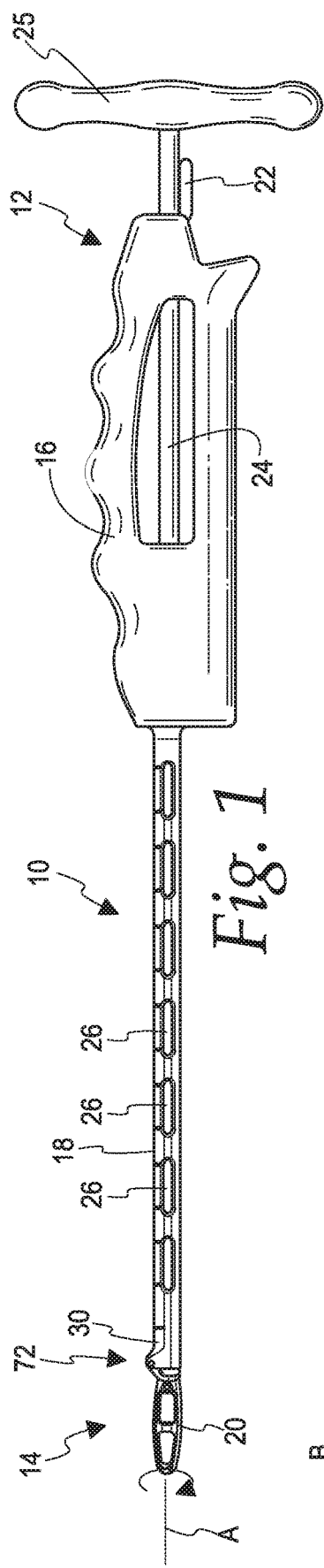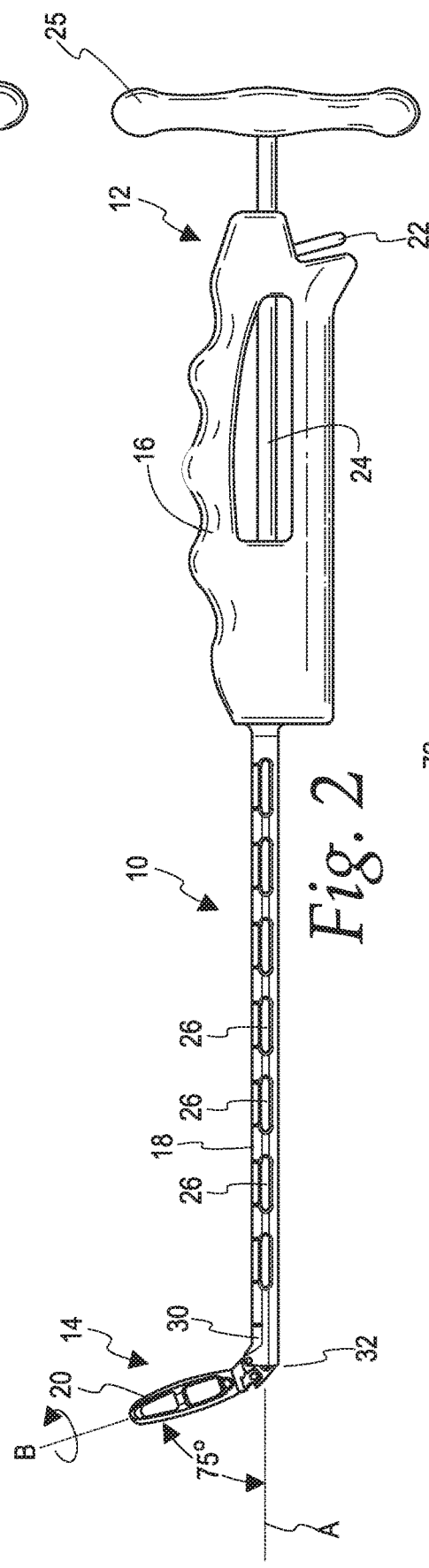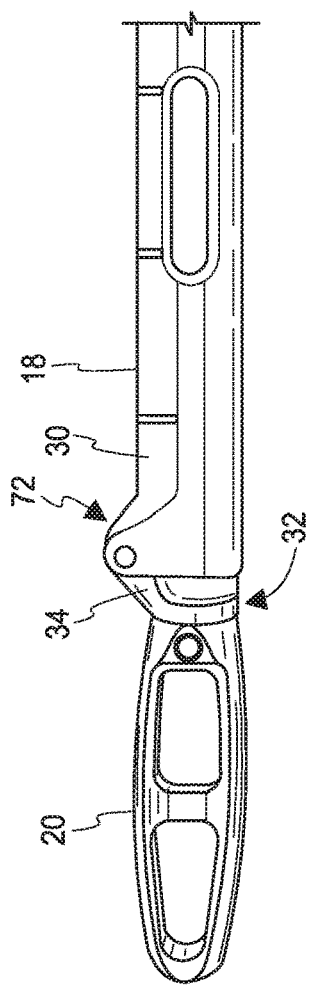

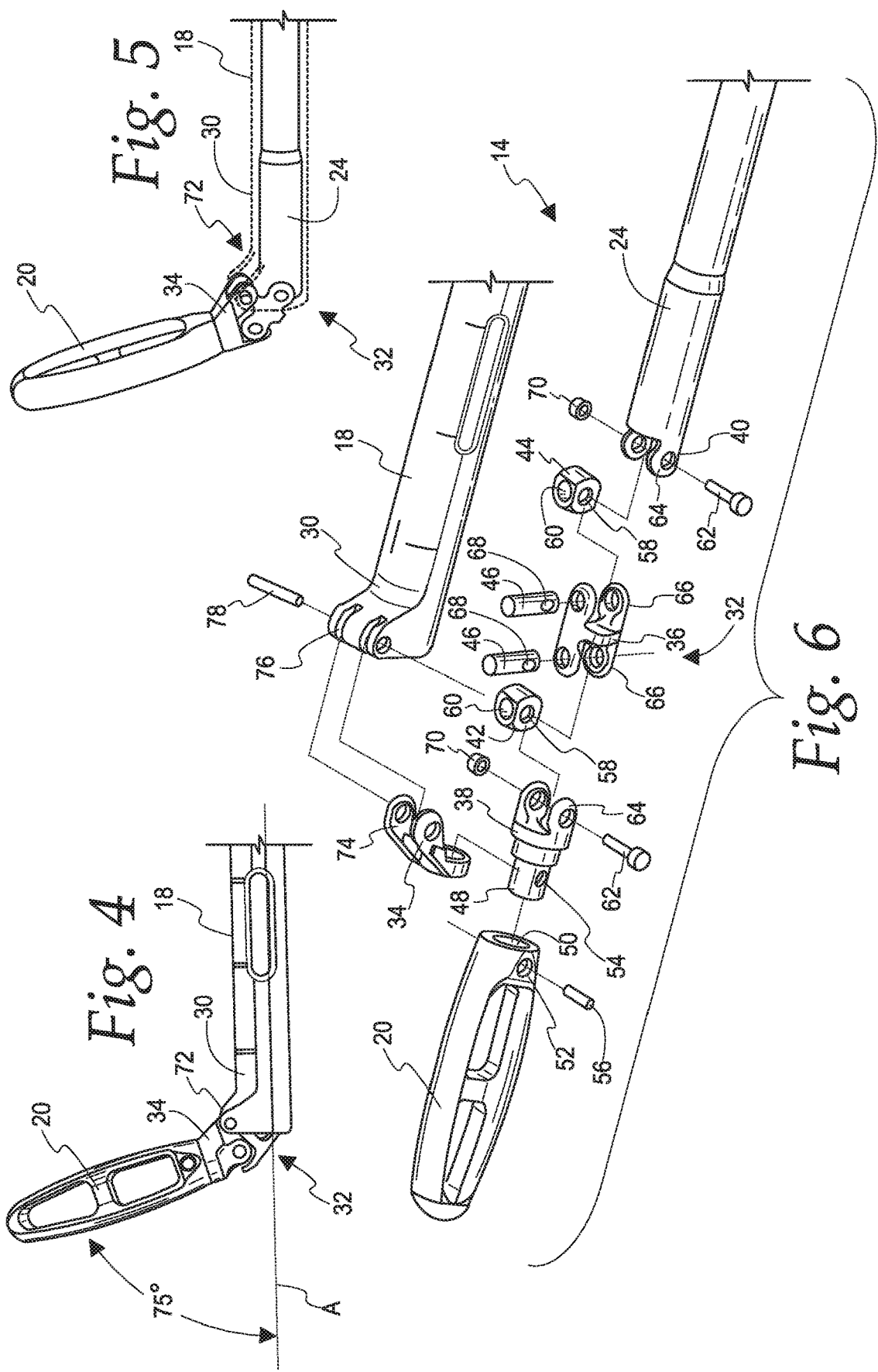

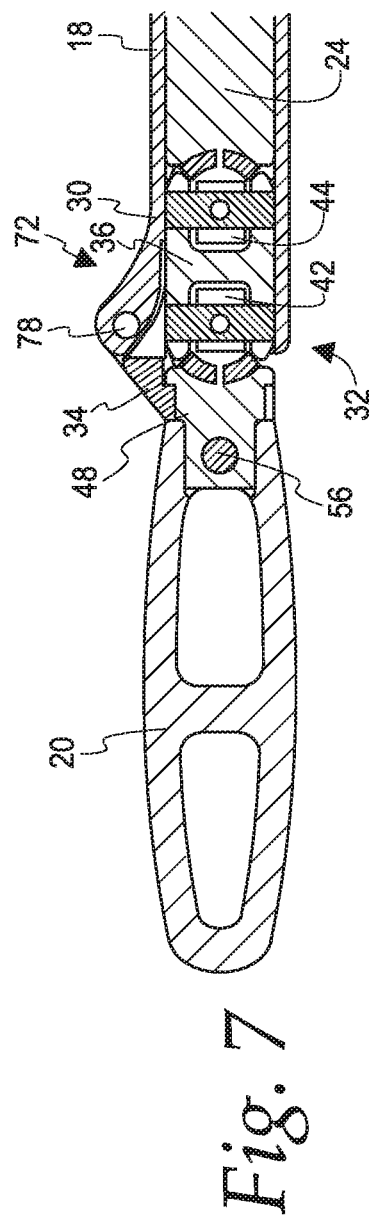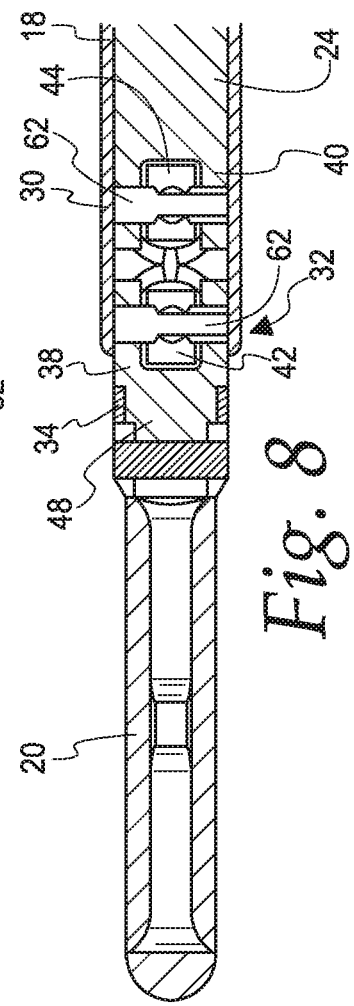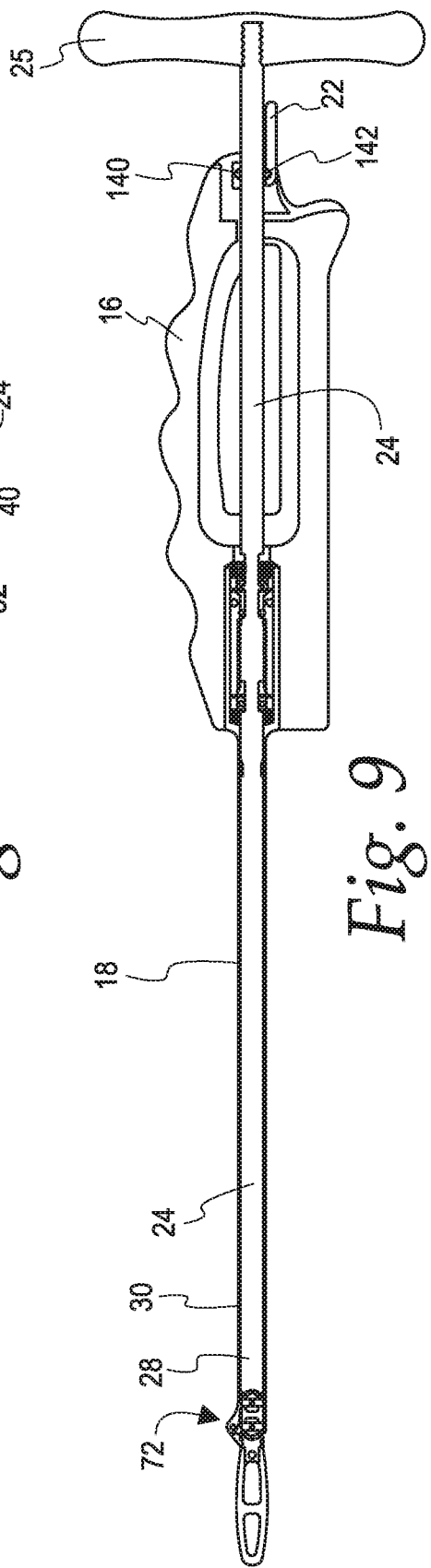

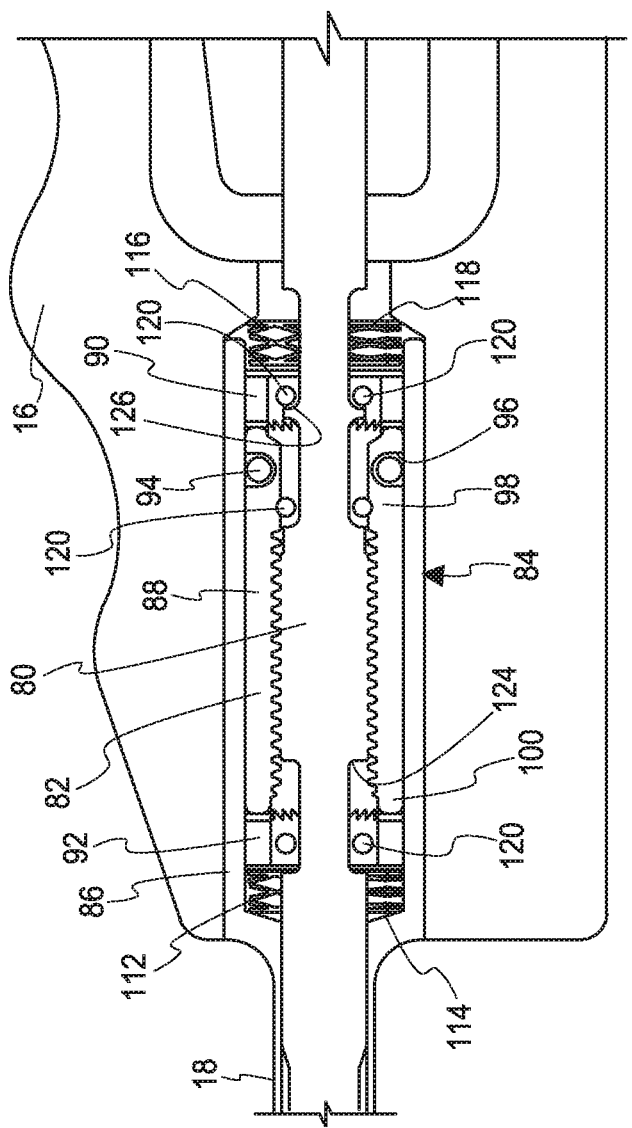
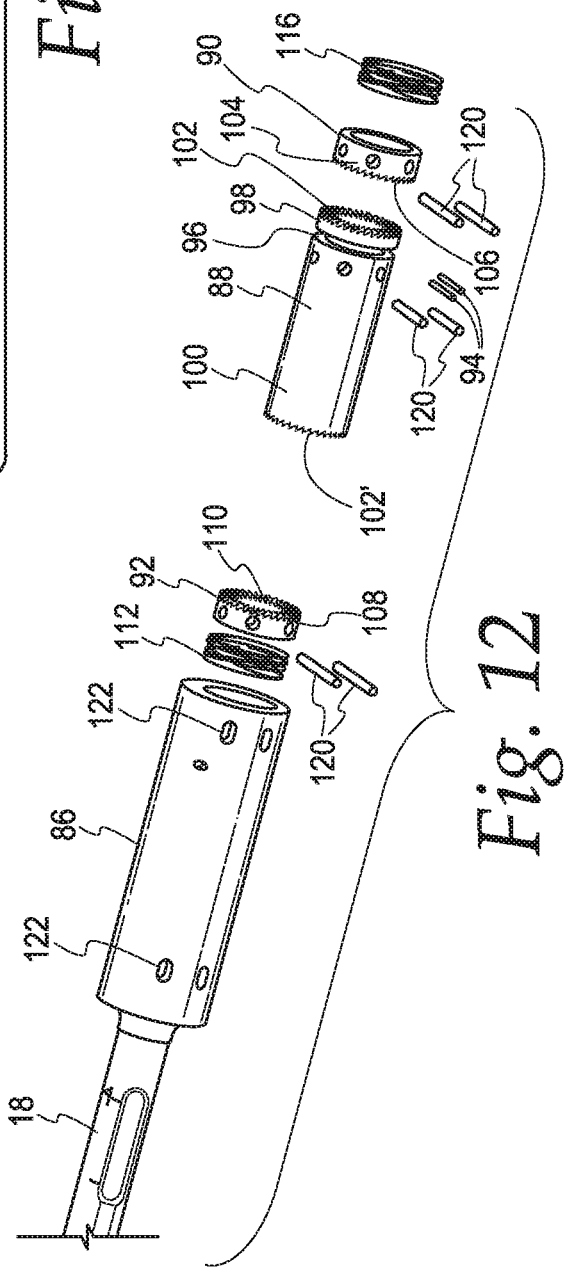

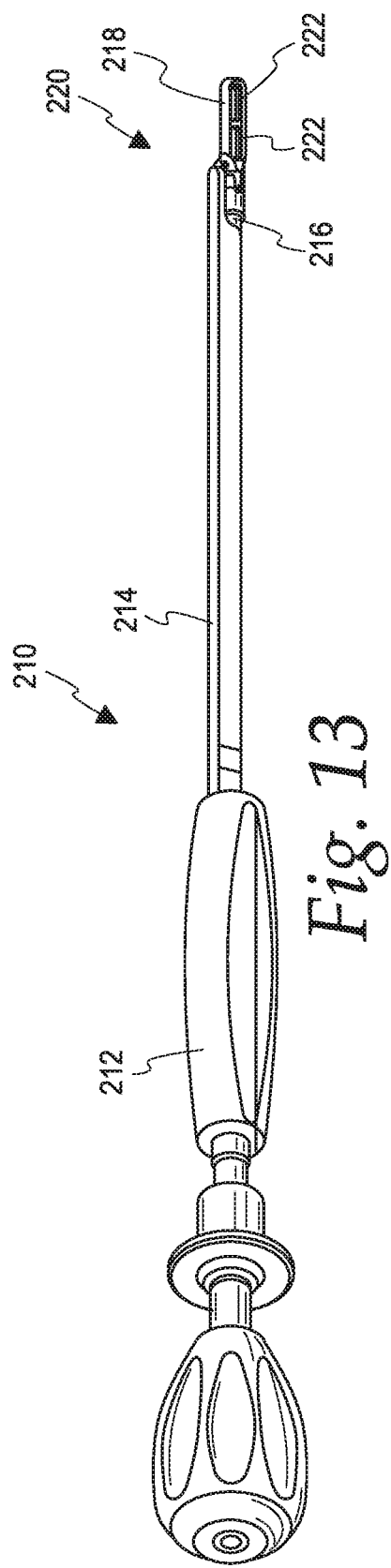
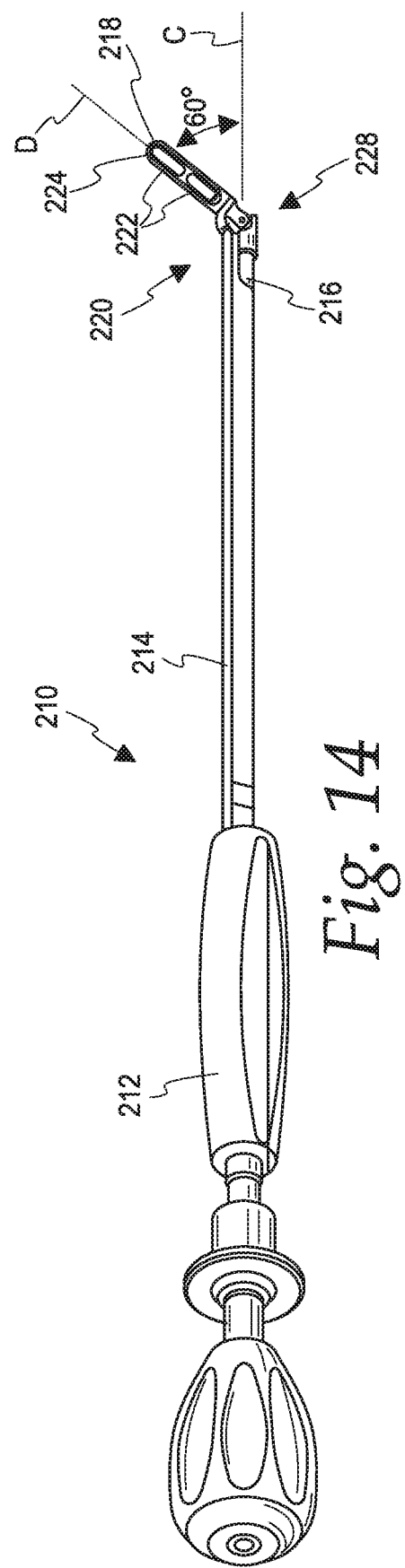

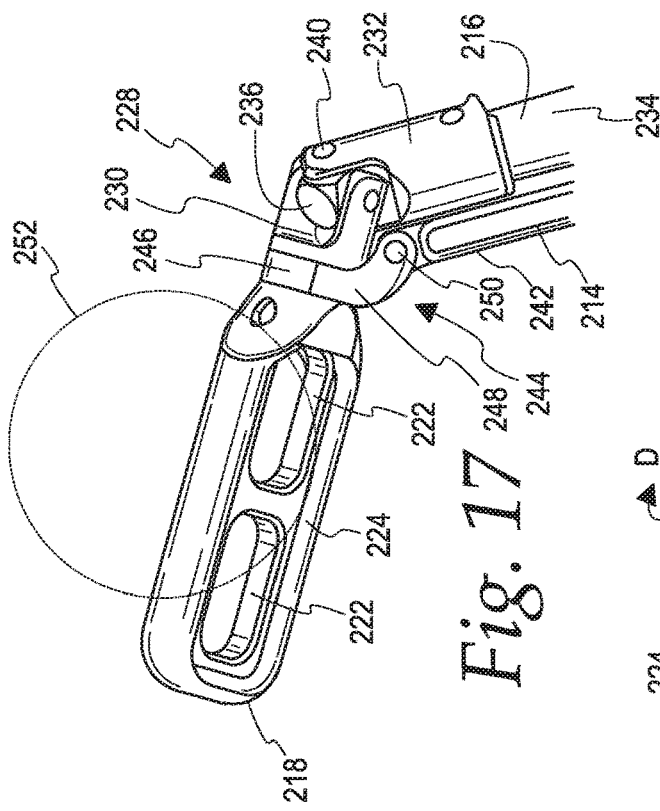
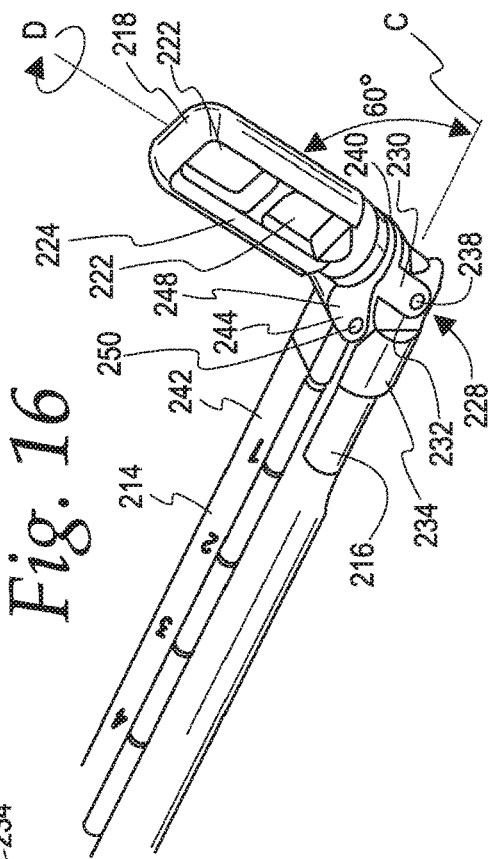
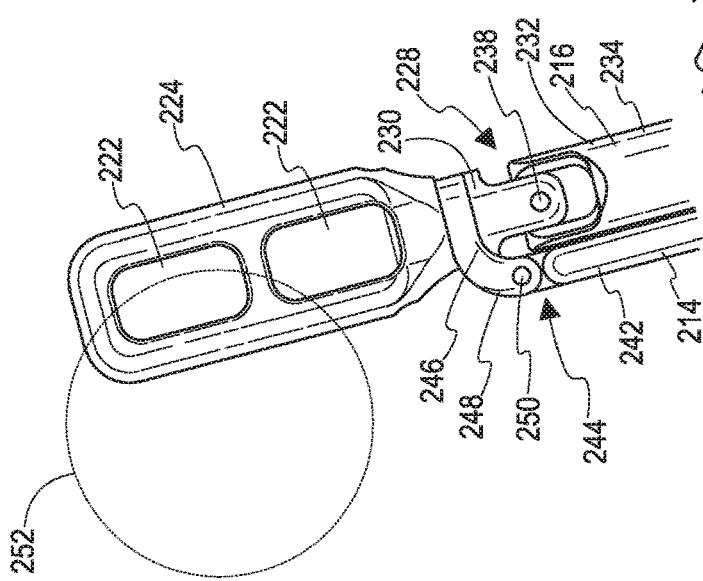

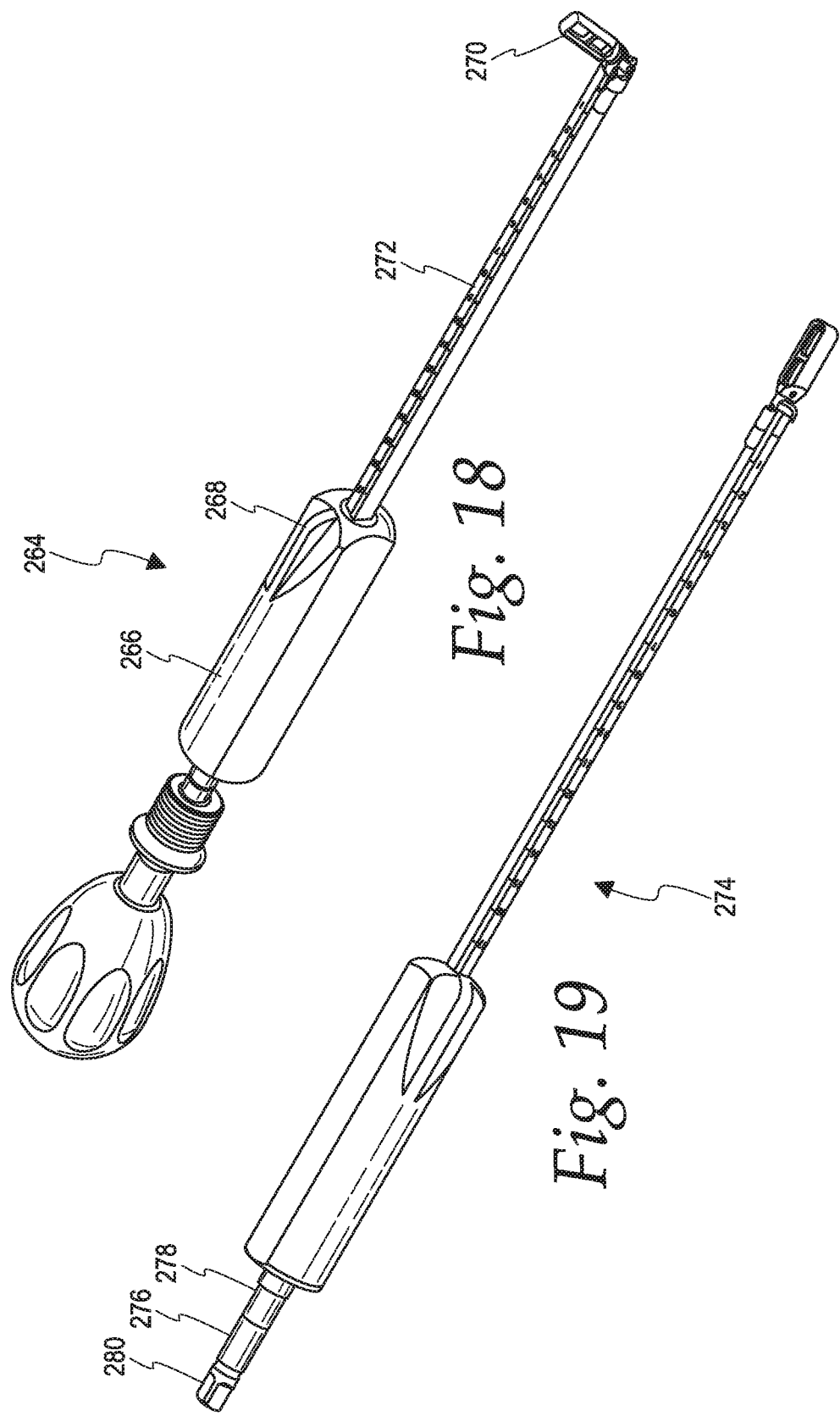

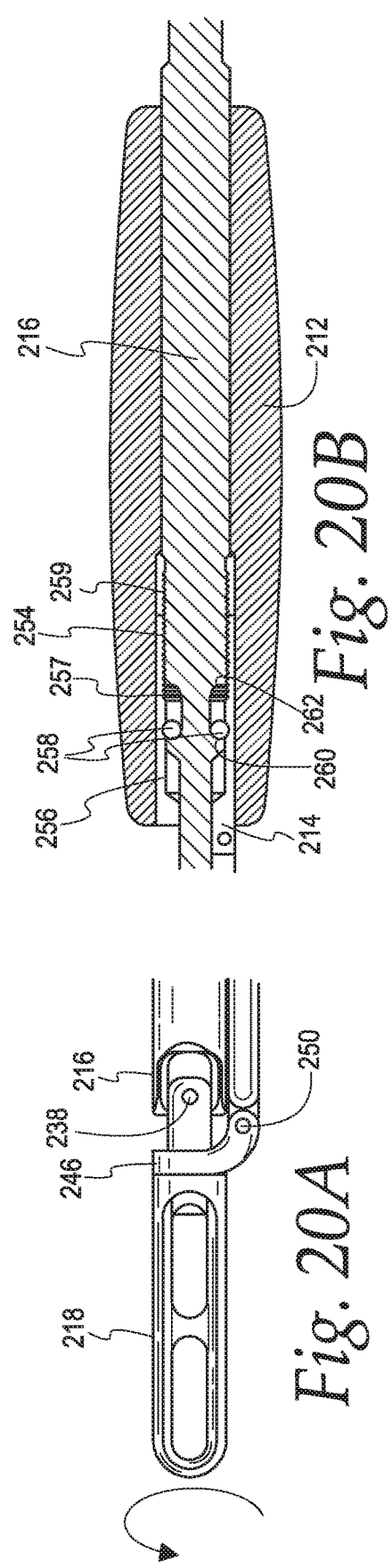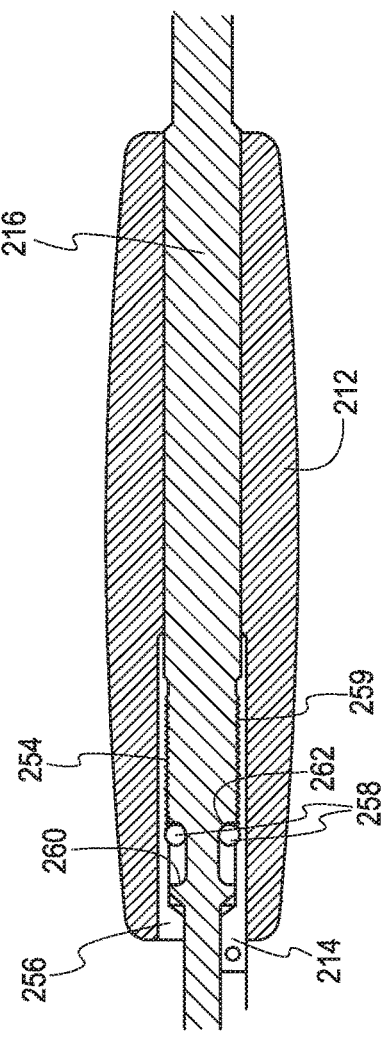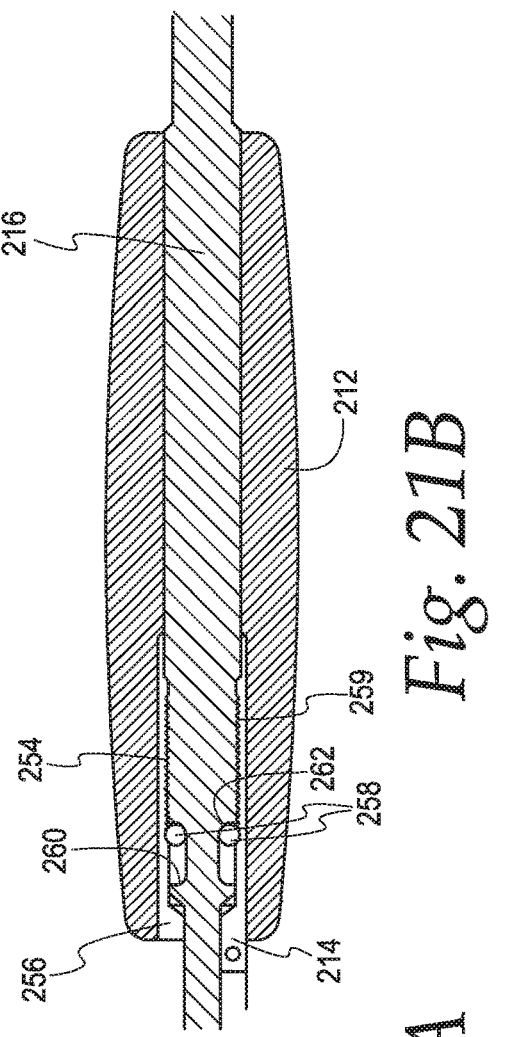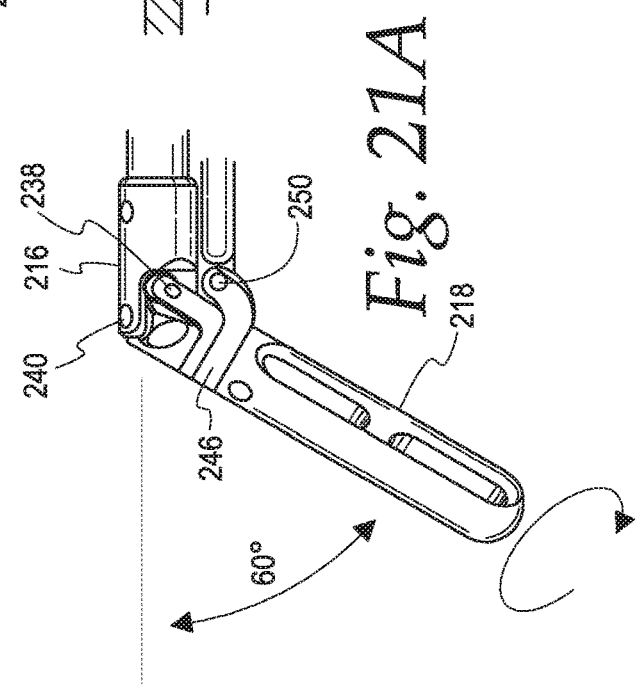
Fig. 20A Fig. 20B
Fig. 21A Fig. 21B

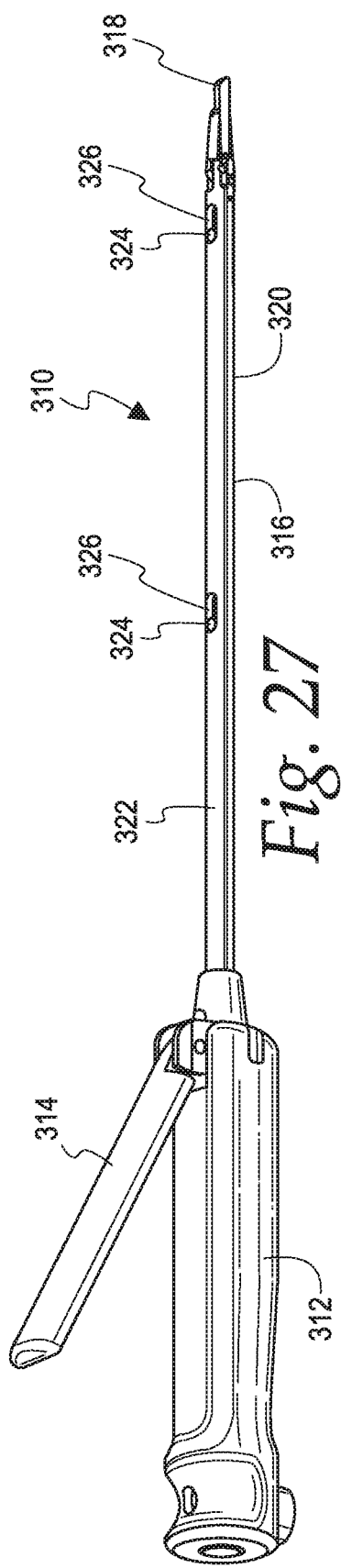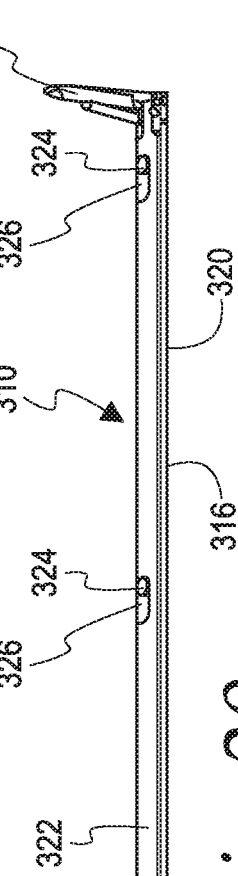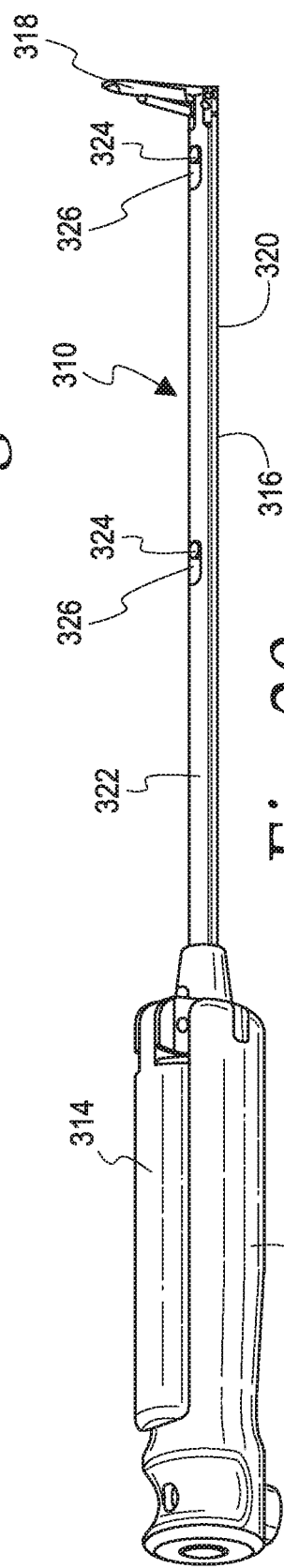

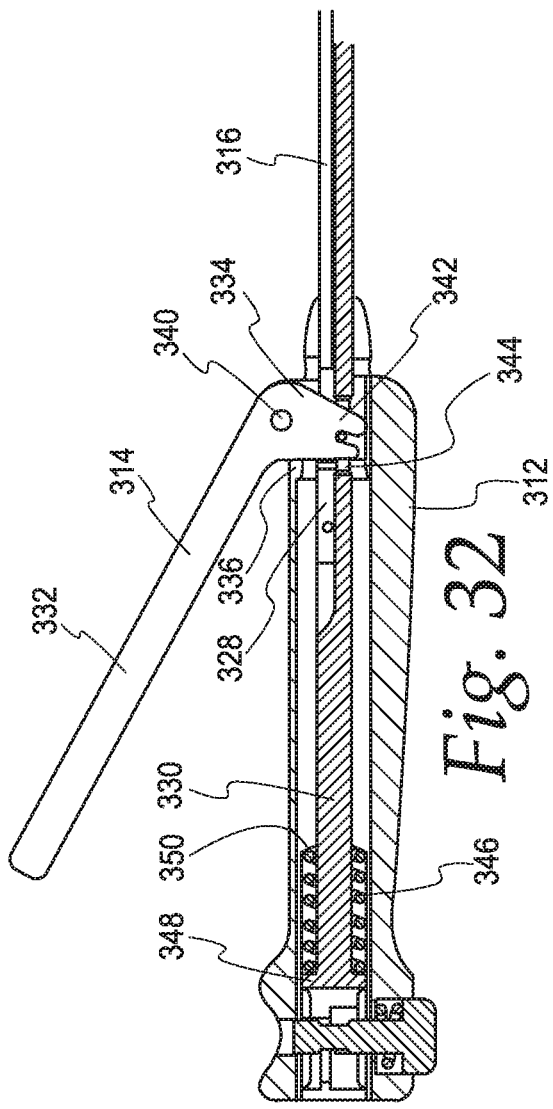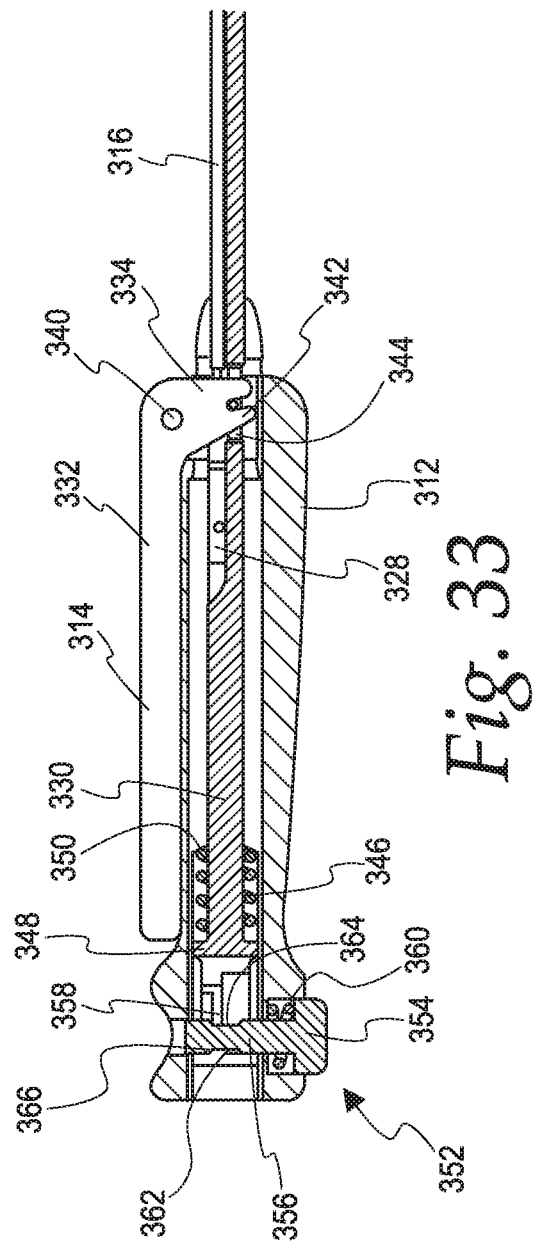

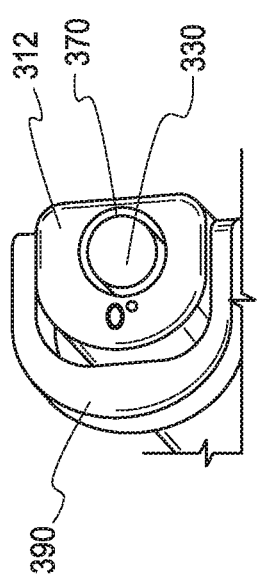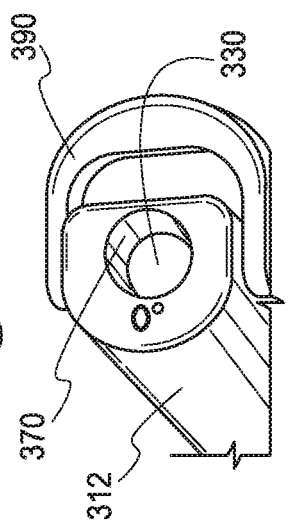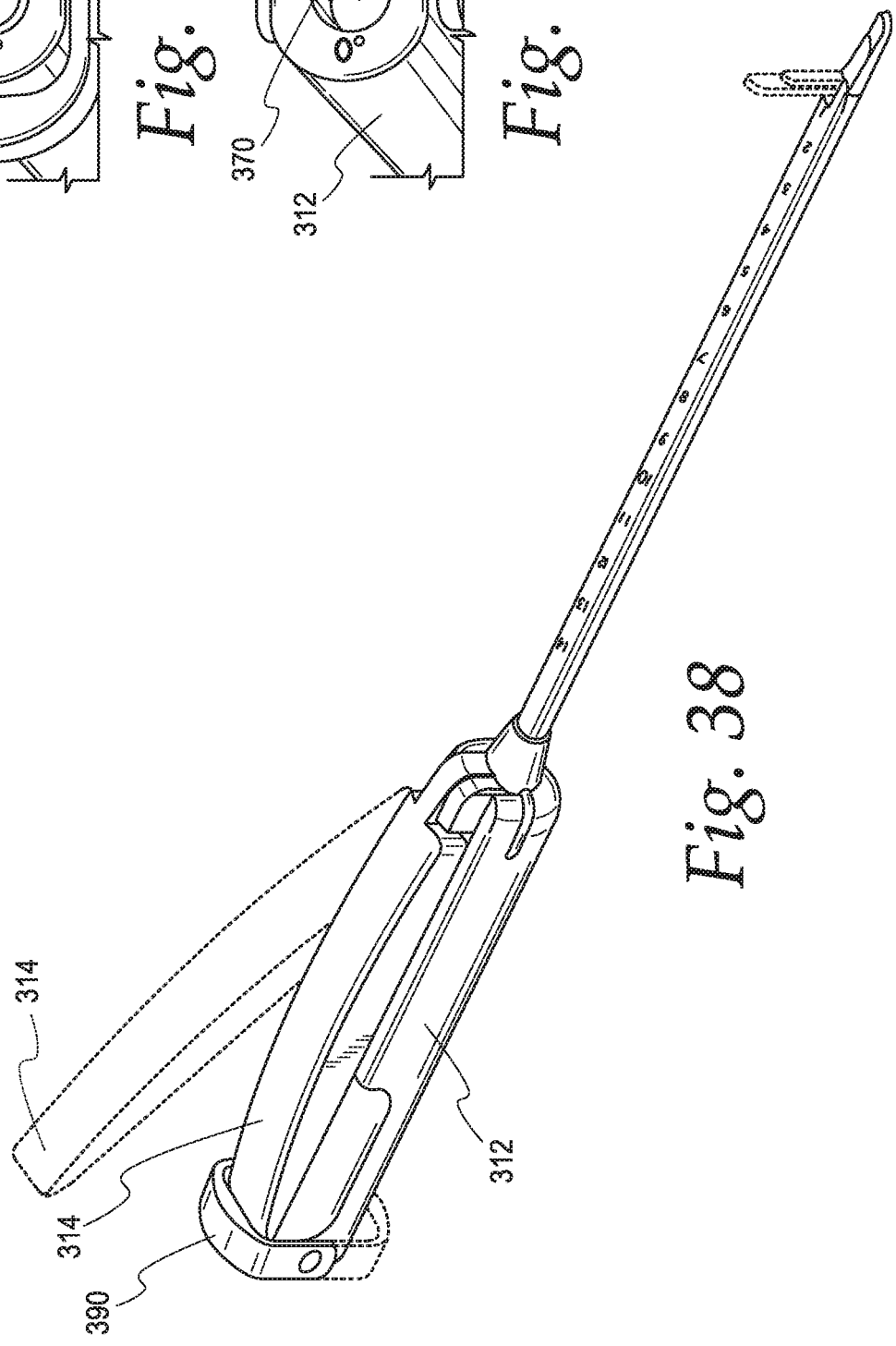

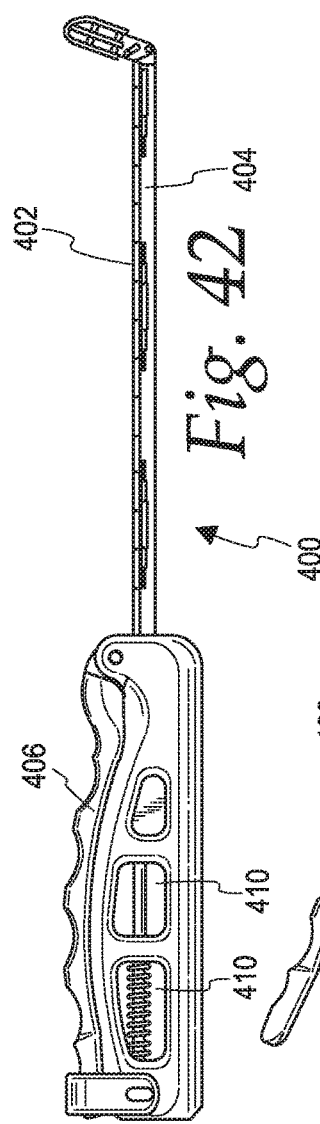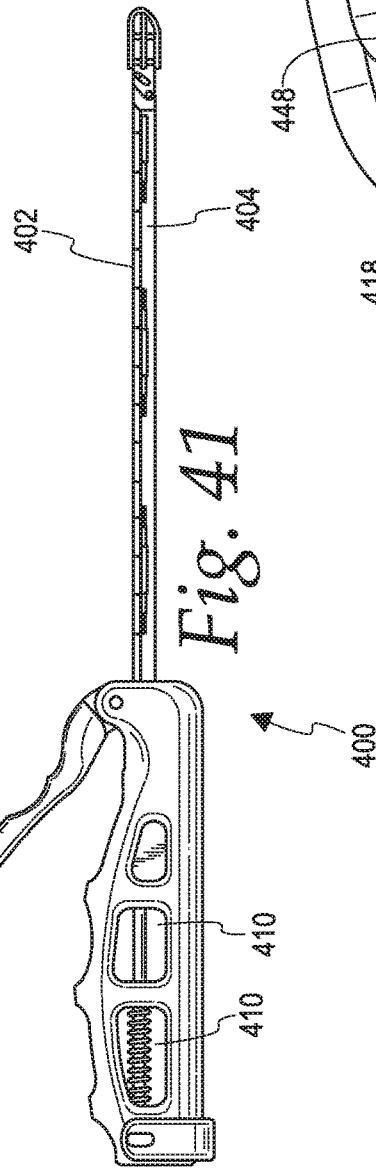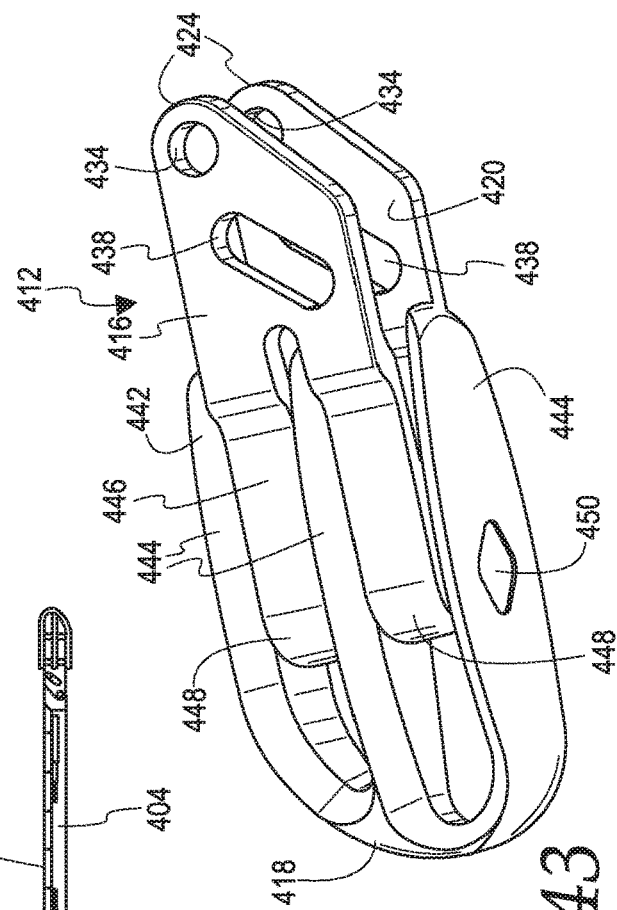

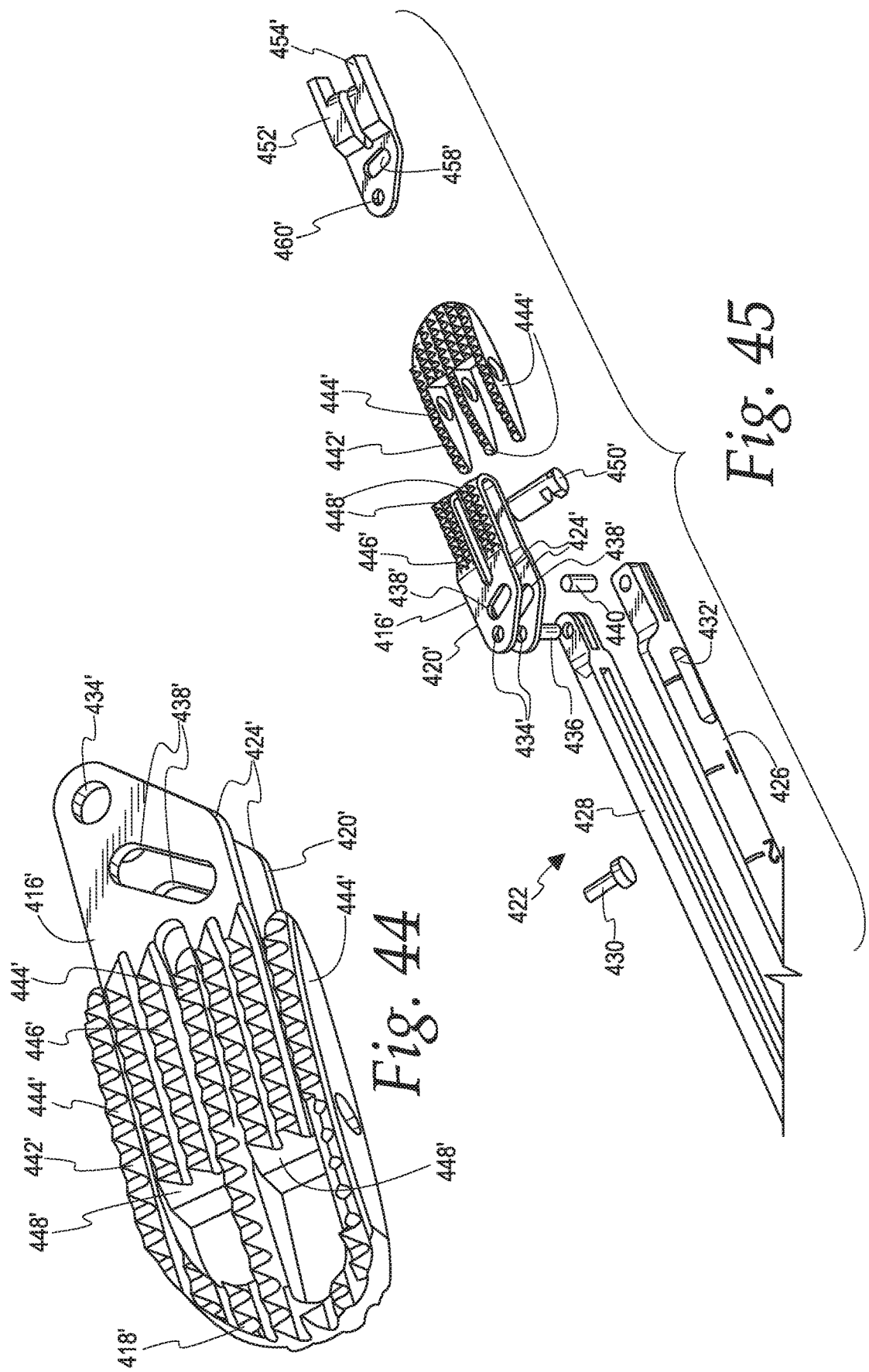

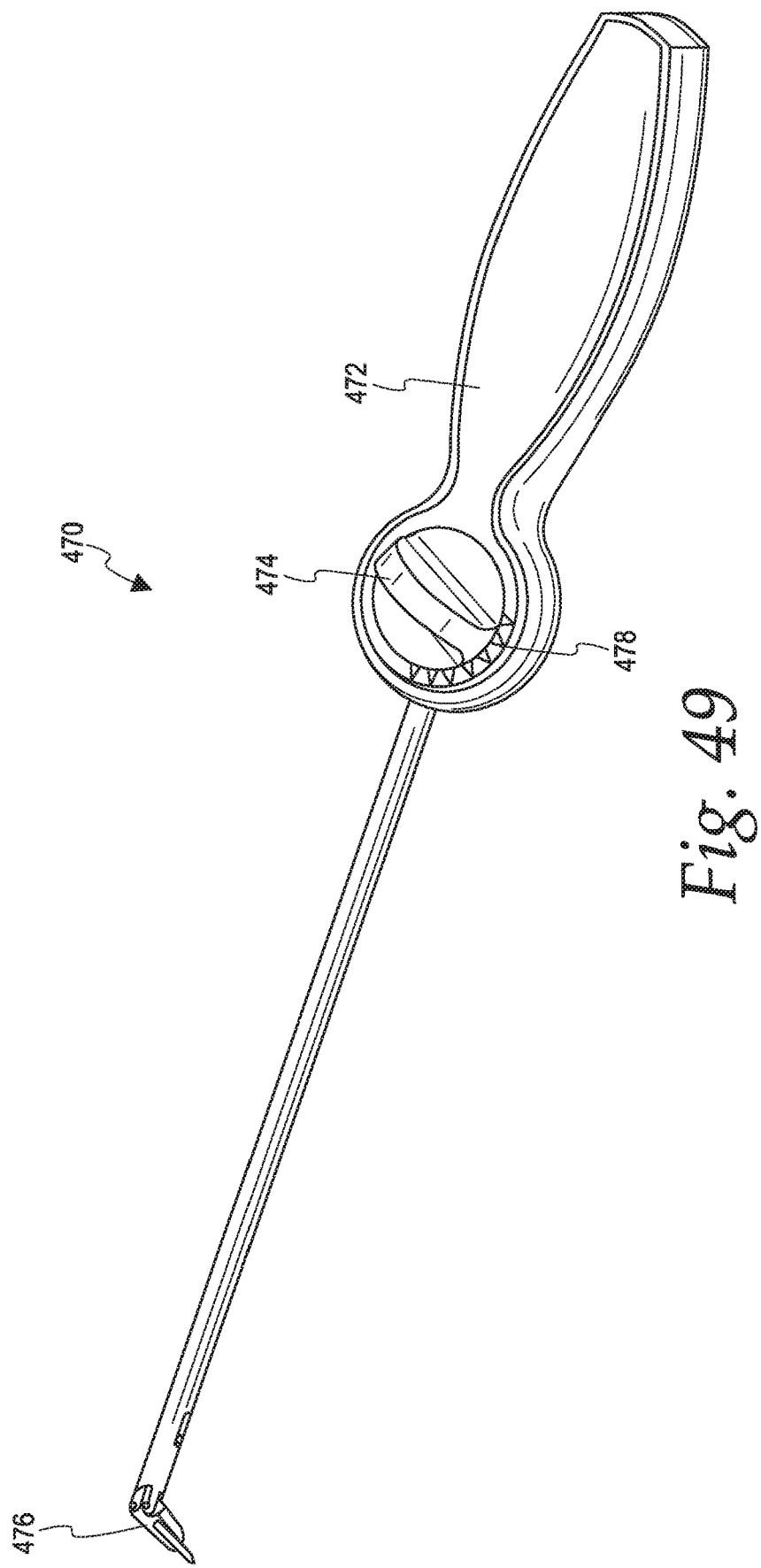

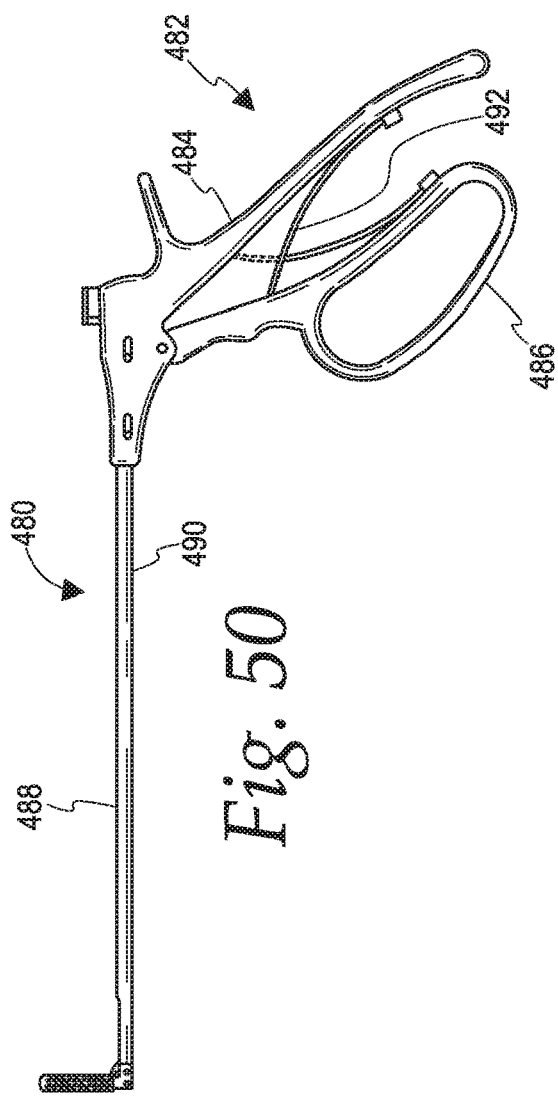
Fig. 50
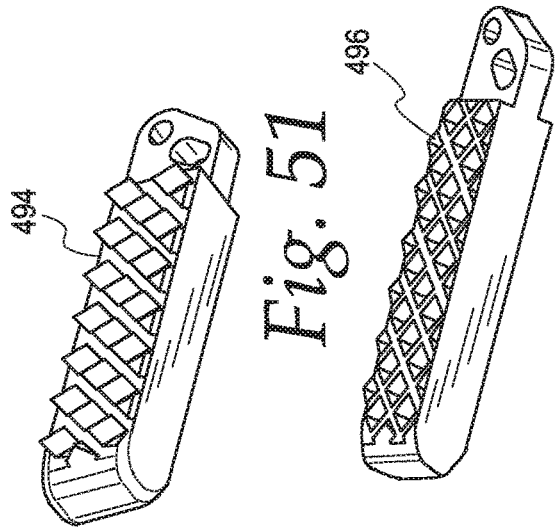
Fig. 51
Fig. 52
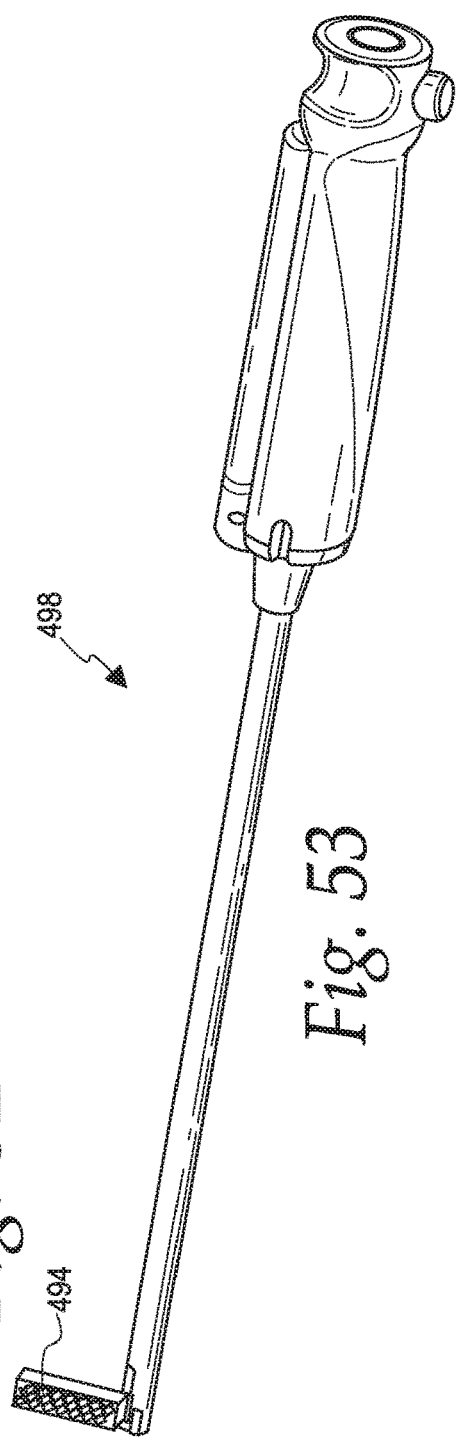
Fig. 53

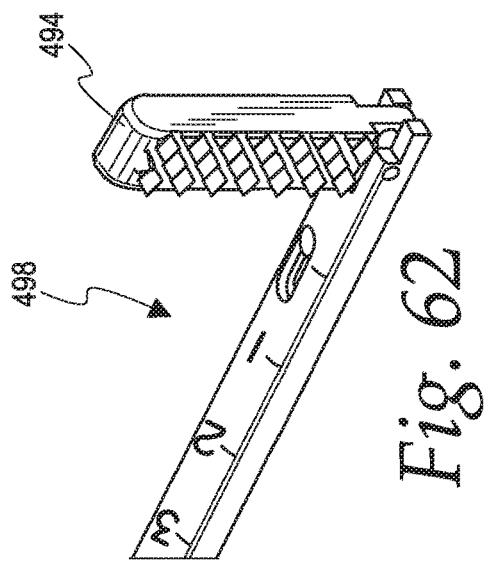
Fig. 59
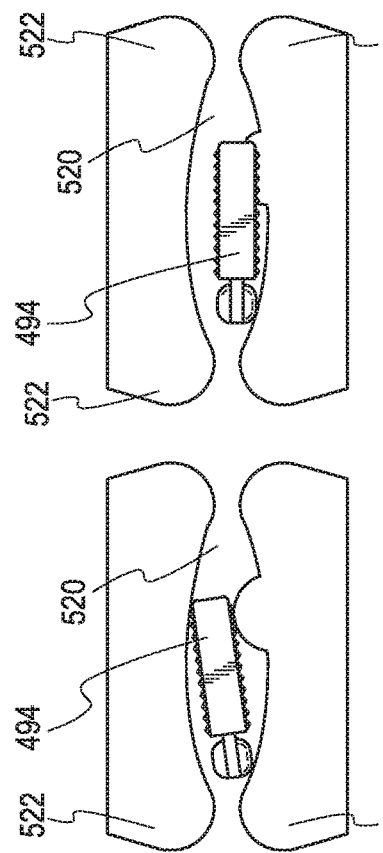
Fig. 62
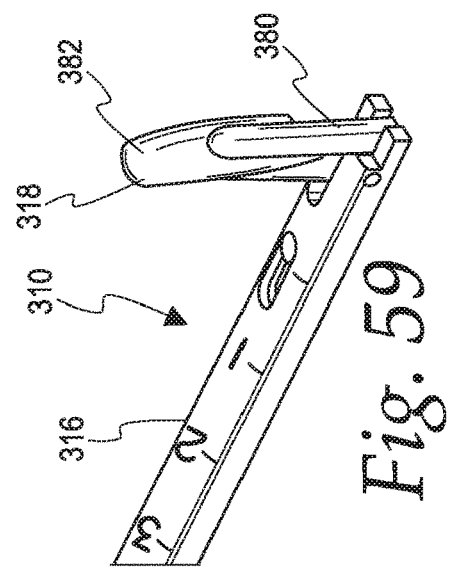
Fig. 60
Fig. 61
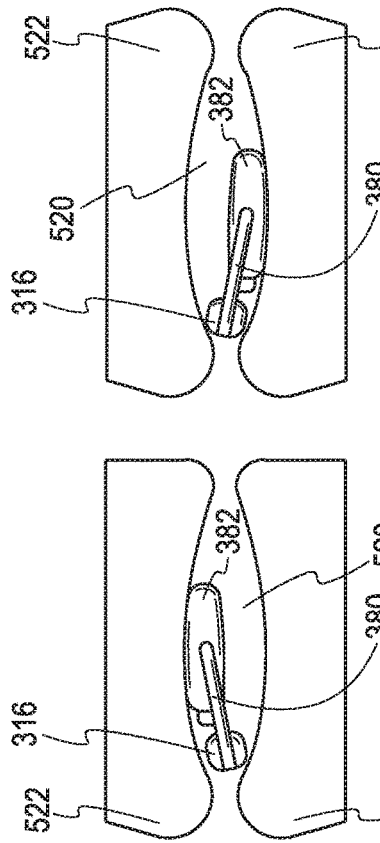
Fig. 63
Fig. 64

ARTICULATED INSTRUMENTATION AND METHODS OF USING THE SAME

The present application is a continuation of International PCT Application No. PCT/US19/22632, filed Mar. 15, 2019, which claims the benefit of and priority to U.S. Provisional Patent Application No. 62/644,101, filed Mar. 16, 2018, both of which are hereby incorporated herein by reference.

FIELD OF THE DISCLOSURE

The subject matter of the present disclosure generally relates to articulated instruments and systems for cutting and removing tissue, and more particularly, to instruments and systems for preparing the disc space for deployment of an implant into the disc space. The subject matter also relates to preparing the disc space in minimally invasive surgical (MIS) methods with reduced tissue and bone distraction or removal.

BACKGROUND

The benefits of interbody fusion have been well described in the literature and include both direct and indirect decompression of the neural elements, as well as, a high rate of bony fusion. A number of approaches have been described to achieve interbody fusion of the lumbar spine (posterior, anterior and lateral) each with a unique set of advantages and challenges. Looking at the posterior approach, some of the challenges to provide for a good fusion have been the discectomy and the disc space preparation. Traditionally, discectomy are performed with the use of simple manual instruments, such as shavers, curettes, pituitary rongeurs and rasps.

For a typical posterior surgical approach, an incision is made through the back of the patient and access to the disc space is achieved. As surgeons want to take advantage of minimally invasive surgery (MIS), the access opening to the disc is becoming smaller and smaller and therefore, traditional manual straight or curved instruments are not always possible to use and the present disclosure provides embodiments, apparatus and methods to address those challenges and to improve on the advantages of MIS.

SUMMARY

The articulated instruments, systems and methods may be used to prepare the disc space for the implantation of fusion implants or disc replacement implants. For example, the instruments, systems and methods disclosed herein may be used in conjunction with the Luna® Interbody device sold by Benvenue Medical, Inc. of California, as well as other devices and implant. Such devices and implants may also include those disclosed in U.S. Application No. 62/623,025, filed Jan. 29, 2018 and U.S. Pat. Nos. 8,454,617 and 9,480,574, which are hereby incorporated herein by reference.

The present disclosure generally relates to articulated instrumentation and a first aspect of the disclosure relates to an articulated paddle shaver that combines rotatory motion and angular motion in a single instrument to allow for a broader area of tissue disruption.

Another aspect of the disclosure relates to angular deflection of tip instruments to reach areas that are up to a perpendicular location away from the entry axis.

Another aspect of the disclosure relates to a pivot mounted like end effector to better aligned with the endplate to provide a more adapted contact area.

A further aspect of the disclosure relates to the different articulated mechanism used to control tip deflection with squeezable levers or rotating knobs.

Yet another aspect of the disclosure relates to an articulated disc preparation instrument including a handle having a proximal end and a distal end. The instrument also includes an outer shaft extending from the distal end of the handle and an inner shaft extending within the outer shaft. The instrument further includes a disruption tool hingedly attached to the distal end of the inner shaft and hingedly attached the distal end of the outer shaft. When the inner shaft is rotated, the disruption tool rotates with the inner shaft, and when the inner shaft is moved linearly relative to the outer shaft, the disruption tool moves between a first straight configuration wherein an axis of the disruption tool is parallel to an axis of the outer shaft and a second angled configuration wherein the tool is at an angle relative to the outer shaft through a range of angles up to 120°. In one embodiment, the range of angles may be up to 60° and beyond. In another embodiment, the range of angles may be up to 75°.

A further aspect of the disclosure relates to an articulated disc preparation instrument including a handle having a proximal end and a distal end. The instrument further includes an outer shaft extending from the distal end of the handle and an inner shaft extending within the outer shaft. The instrument also includes a disruption tool hingedly attached to the distal end of the inner shaft and hingedly attached the distal end of the outer shaft. The disruption tool rotates with the inner shaft, and when the inner shaft is moved linearly relative to the outer shaft, the disruption tool moves between a first straight configuration wherein an axis of the disruption tool is parallel to an axis of the outer shaft and a second angled configuration. The instrument includes a free spin drive mechanism that that linearly advances the inner shaft when the inner shaft is rotated. The inner shaft continues to rotate when the drive shaft reaches a proximal travel limit and a distal travel limit.

Yet another aspect relates to an articulated disc preparation instrument including a handle having a proximal end and a distal end. The instrument also includes a shaft extending from the distal end of the handle, wherein the shaft includes an upper half shaft and a lower half shaft. The upper half shaft selectively moveable linearly relative to the lower half shaft. The instrument includes a disruption tool hingedly attached to the upper half shaft and hingedly attached to the lower half shaft. When the lower half shaft is moved linearly relative to the upper half shaft, the disruption tool moves between a first straight configuration wherein an axis of the disruption tool is parallel to an axis of the shaft and a second angled configuration. The instrument also includes a lever pivotally connected to the handle and operatively connected to the lower half shaft so that moving the lever relative to the handle results in moving the lower half shaft linearly relative to the upper half shaft.

These and others aspects will be apparent from the following description.

BRIEF DESCRIPTION OF THE FIGURES

FIG. 1 is a side elevational view of one embodiment of an articulated instrument in accordance with the present disclosure, shown in a straight configuration;

FIG. 2 is a side elevational view of the articulated instrument of FIG. 1, shown with the tip in an angled configuration;

FIG. 3 is a side elevational view of the distal end of the articulated instrument of FIG. 1;

FIG. 4 is a side elevational view of the distal end of the articulated instrument of FIG. 1;

FIG. 5 is a perspective view of the distal end if the articulated instrument of FIG. 1, showing portions of the u-joint and the shaver in an articulated position that may be up to 120°;

FIG. 6 is an exploded view of the distal end of the articulated instrument of FIG. 1;

FIG. 7 is a cross-sectional view of the distal end of the articulated instrument of FIG. 1;

FIG. 8 is a cross-sectional view of the distal end portion of the articulated instrument of FIG. 1;

FIG. 9 is a cross-sectional view of the articulated instrument of FIG. 1;

FIG. 11 is a partial cross-sectional view of the handle of the articulated instrument of FIG. 1 that includes one embodiment of a free spin mechanism that may be employed in any of the articulated instruments of the present disclosure;

FIG. 12 is an exploded view of that free spin mechanism of FIG. 11;

FIG. 13 is a perspective view of another embodiment of an articulated instrument in accordance with the present disclosure, shown in a straight configuration;

FIG. 14 is a perspective view of the articulated instrument of FIG. 13, shown with the tip in an angled configuration;

FIG. 15 is a perspective view of the working end or tool of the articulated instrument shown in a straight orientation:

FIGS. 16 & 17 are perspective views of the working end or tool of the articulated instrument of FIGS. 13-16 shown in an angular orientation;

FIG. 18 is a perspective view of another embodiment of the articulated instrument of the present disclosure wherein the instrument includes markings and an orientation indicator;

FIG. 19 is a perspective view of an articulated instrument without a distal handle attached to the inner shaft;

FIG. 20A is side elevation view of the distal end of the articulated instrument with the working end or tip in a straight configuration;

FIG. 20B is a cross-sectional view that shows the relative position of the inner shaft within the internal mechanism of the handle;

FIG. 21A is perspective view of the distal end of the articulated instrument with the working end or tip in a straight configuration;

FIG. 21B is a cross-sectional view that shows the relative position of the inner shaft within the internal mechanism of the handle;

FIG. 27 is a side elevation view of another embodiment of an articulated instrument of the present disclosure, shown with the distal end in a straight configuration;

FIG. 28 is a side elevation view of the articulated instrument of FIG. 27, shown with the distal end in a straight configuration;

FIG. 29 is a perspective view of one embodiment of a blade of the articulated instrument of FIG. 27;

FIG. 30 is a side elevation view of the articulated instrument of FIG. 27, shown with the distal end in an angled configuration;

FIGS. 32 and 33 are cross-sectional views of the handle of the instrument of FIG. 27;

FIG. 38 is a perspective view of another embodiment of an articulated instrument;

FIGS. 39 and 40 are perspective views of proximal end of the instrument of FIG. 27;

FIG. 41 is a perspective view of another embodiment of an articulated instrument;

FIG. 42 is a perspective view of the articulated instrument of FIG. 41, shown with the tool in an angled configuration;

FIG. 43 is a perspective view of one embodiment of a tool;

FIG. 44 is a perspective view of another embodiment of a tool;

FIG. 45 is an exploded view of the distal end of the articulated instrument of FIG. 27, shown with the tool of FIG. 44;

FIG. 49 is a perspective view of another embodiment articulated instrument shown in a straight configuration;

FIG. 50 is a plan view of another embodiment of an articulated instrument;

FIG. 51 is a perspective view another embodiment of a tool;

FIG. 52 is a perspective view another embodiment of a tool;

FIG. 53 is a perspective view of another embodiment articulated instrument;

FIG. 59 is a perspective view of a distal end of one embodiment of an articulated instrument in an angled configuration;

FIGS. 60 and 61 are schematic views showing the distal end of the articulated instrument of FIG. 59 within a disc space;

FIG. 62 is a perspective view of a distal end of one embodiment of an articulated instrument in an angled configuration;

FIGS. 63 and 64 are schematic views showing the distal end of the articulated instrument of FIG. 62 within a disc space;

DETAILED DESCRIPTION

Figure 10:
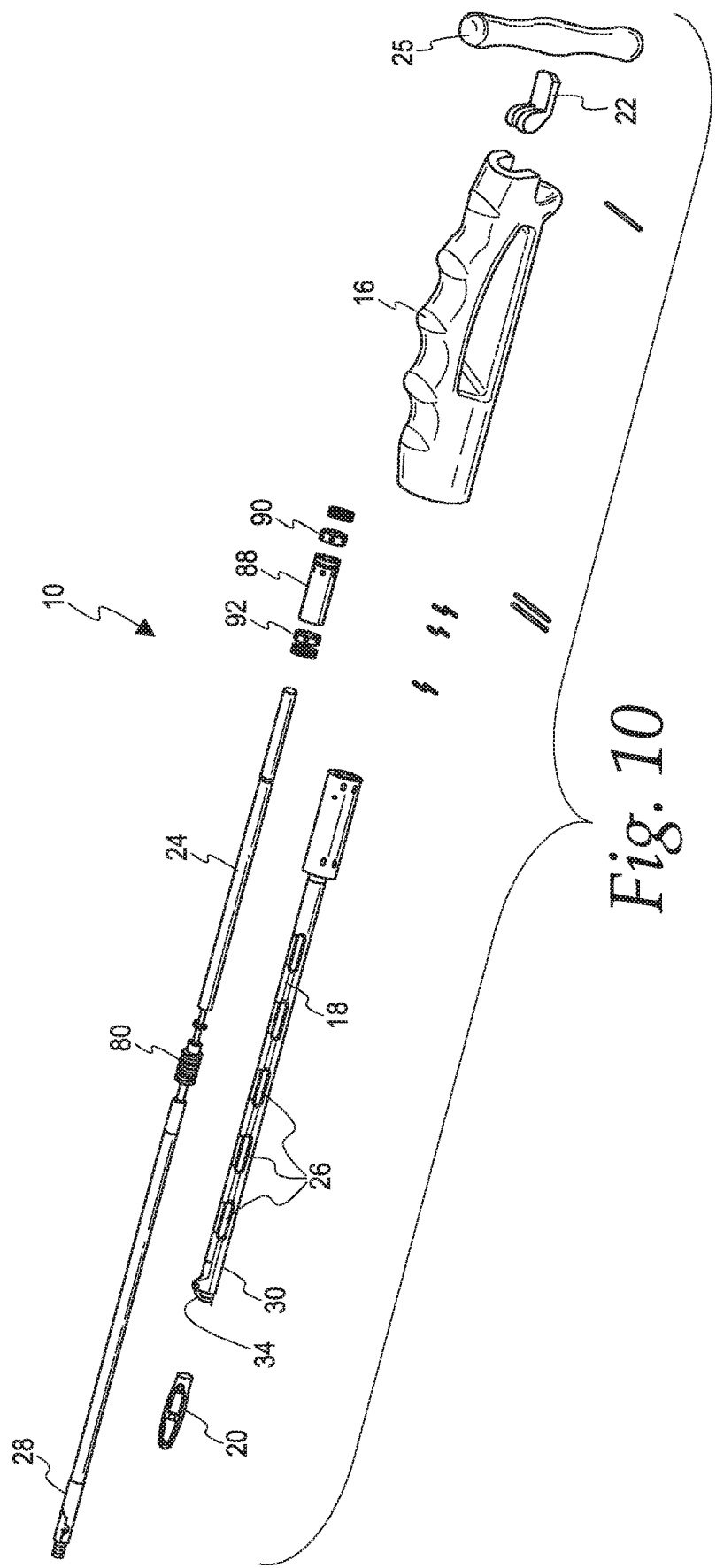
FIG. 10 is an exploded view of the articulated instrument of FIG. 1.

Turning to FIGS. 1 and 2, there is shown one embodiment of an articulated instrument 10. Generally, the articulated instrument 10 includes a proximal end 12 and a distal end 14. At the proximal end 12 of the instrument 10 is a handle 16, and an outer shaft 18 extends from the distal end of the handle 16. A disruption tool 20, such as a blade, shaver, rasp or any other suitable tool, may be located at the distal end 14 of the articulated instrument 10. The distal end 14 of instrument 10 may be inserted into the disc space between adjacent vertebrae and used to disrupt (cut, scrape, etc.) tissue within a disc space. For example, depending on the tool, the instrument 10 may be used to cut disc tissue and/or scrape endplates. The disruption tool 20 may be articulated so as to move the tool 20 between a straight configuration (as shown in FIG. 1), and an angled configuration relative to the axis A of the outer shaft 18 (as shown in FIG. 2). Furthermore, the tool 20 also may be rotated about axis B (FIG. 2) of the tool 20 as the tool is moved between the straight and angled configurations. The instrument 10 may also include an orientation indicator, which indicates the angled position of the tool 20 relative to the axis of the outer shaft 18 during use. In the illustrated embodiment, the indicator includes an orientation tab 22 associated with handle 16. As shown in FIG. 1, the tab 22 is located in a first position when the tool 20 is in a straight configuration, and moves to a second position, as shown in FIG. 2, as the tool 20 moves into an angled configuration. The tab 22 may indicate the orientation of the tool 20 throughout the movement between the straight configuration and the angled configuration. This allows the user to position the tool at a selected angle.

Referring now to FIGS. 9 and 10, FIG. 9 shows a cross-sectional view of the instrument 10 and FIG. 10 shows an exploded view. As mentioned above, the instrument 10 includes a handle 16 and an outer shaft 18 extending from the handle. The instrument 10 also includes an inner shaft (drive shaft) 24 which extends through the handle 16 and the outer shaft 18. A knob 25 may be associated with the proximal end of the inner shaft 24 wherein the knob 25 may be gripped and turned by the user to rotate to shaft 24. The outer shaft 18 may be generally cylindrical or have a generally rectangular cross-section that substantially surrounds the inner shaft 24. In another embodiment, the outer shaft 18 may at least partially surround the inner shaft 24. For example, the outer shaft 18 may have a semi-circular cross-section that is positioned around the inner shaft 24. In the illustrated embodiment, the outer shaft 18 includes windows 26 (FIGS. 1 and 2), which allows for easy of cleaning of the shafts.

Referring to FIGS. 3-6, 9 and 10, the tool 20 of instrument 10 is operably attached to the distal end 28 of the inner shaft 24 and the distal end 30 of the outer shaft 18 in a manner that allows the tool 20 to both move into an angled configuration and simultaneously rotate about its axis. For example, the tool 20 may initially be in a straight configuration as illustrated in FIG. 3. When the inner shaft 24 moves linearly in a distal direction within the outer shaft 18 and handle 16, the tool 20 moves into an angled configuration. When the inner shaft 24 moves linearly in a proximal direction, the tool 20 moves into the straightened configuration. In one embodiment, the tool 20 may be moved into any position that is between 0° and 120° relative to the axis A of the outer and inner shafts 18, 24. In another embodiment, the tool 20 may be positioned up in at a ranges of angles up to 75°, and in another embodiment, the tool may be positioned at a range of angles up to 60° relative to the axis A of the outer and inner shafts 18, 24. In yet another embodiment the tool may be positioned at a range up to 60° and beyond. Furthermore, rotating the inner shaft 24 results in the tool 20 rotating about its axis B.

In one embodiment, the tool 20 is hingedly connected to the inner shaft 24 by a universal joint (u-joint) 32 that translates rotational movement from the inner shaft 24 to the tool 20 to rotate the tool about its axis. In the illustrated embodiment, the tool 20 is connected to the inner shaft by a double u-joint or a double Cardan joint. Additionally, a hinged lever joint 72 hingedly connects the tool 20 to the distal end 30 of the outer shaft 18. In the illustrated embodiment the hinged lever joint includes a collar 34. FIG. 6 illustrates an exploded view of the distal end 14 of the instrument 10 (FIG. 1), u-joint 32 and hinged joint. FIGS. 7 and 8 illustrate a cross-section of the distal end 14 of the instrument, u-joint 32 and collar 34. The double u-joint includes a middle yoke 36, a distal yoke 38 and a proximal yoke 40. Two yoke spacers 42 and 44 are used to connect the three yokes together with associated pins 46. The proximal yoke 40 is at the distal end 28 of the inner shaft 24 and the distal yolk 38 is at the proximal end of the tool 20. The proximal yoke 38 may be integral with the inner shaft 24 or may be attached to the inner shaft. The distal yoke 38 may be attached to the tool 20. For example, the distal yoke 38 may include a post 48 extending distally therefrom. The tool 20 may include a bore 50 for receiving the post 48. The post 48 and the tool 50 may each include an opening 52 and 54 for receiving a pin 56 or other attachment member for attaching the tool 20 to the post 48.

Each spacer 42 and 44 is hingedly connected the middle yoke 36 and hingedly connected to its respective proximal yoke 40 or distal yoke 38. In the illustrated embodiment, each spacer 42 and 44 includes a side-to-side bore 58 and a top-to-bottom bore 60. Each space 42 and 44 is connected to its respective proximal yoke 40 or distal yoke 38 by pins 62 that pass through the arms 64 of the yoke 42 and 44 and the side-to-side bore 58 of the respective spacer 42 and 44. Each spacer 42 and 44 is connected to its respective side of the middle yoke 36 by pins 46 that pass through the respective arms 66 of the middle yoke 38 and the top-to-bottom bore 60. In the illustrated embodiment pins 46 include a passageway 68 that allows for the passage of pins 62. Additionally, pins 62 may include a pin cap 70 to hold the pins in place.

As mentioned above, a hinged lever joint 72 operatively connects the tool 20 to the distal end 30 the outer shaft 18. The hinged lever joint 72 may include a collar 34 that is placed around the post 48 of the distal yoke 38. The collar 34 includes one or more arms 74 that are hingedly connected to the distal end 30 of outer shaft 18. In the illustrated embodiment, the collar 34 includes two arms 74 that are inserted into slots 76 of the outer shaft 18 and connected to the outer shaft by pin 78. As the inner shaft 24 is moved distally, the hinged lever joint 72 pivots moving the tool 20 into the angled configuration. The joint 72 also allows the tool to rotate as it is moves through the angled positions.

Referring to FIG. 9-11, the inner shaft 24 includes an external threaded portion 80 which engages and mates with an internal threaded element 82 that may be within the handle 16. The external and internal thread portions 80 and 82 define a drive mechanism 84 that moves the inner shaft 24 linearly in proximal and distal directions within the handle 16 and the outer shaft 18. For example, when the inner shaft 24 is rotated in the clockwise direction, the drive mechanism 84 coverts the rotational movement into linear movement and the inner shaft 24 is advanced distally. Similarly, when the inner shaft 24 is rotated in the counter-clockwise direction, the inner shaft 24 is moved proximally.

Optionally, the drive mechanism 84 may be a free spine drive mechanism that allows the inner shaft 24, and thus the tool 20, to continuously rotate during use and when the inner shaft 24 reaches the end of travel in the proximal and distal directions. Referring to FIGS. 11 and 12, the outer shaft 18 may include an enlarged proximal end 86 that is located within a bore of the distal end of the handle 16. The free spin drive mechanism 84 may be located within the enlarged proximal end 86 of the outer shaft 18. The drive mechanism 84 may include a middle drive sleeve 88, a proximal drive ratchet ring 90 and a distal drive ratchet ring 92. The middle drive sleeve 88 may be held within the enlarged proximal end portion 86 of the outer shaft 18 by pins 94. The outer surface of the middle drive sleeve 88 may include a circumferential groove 96 that engages the pins 94. This prevents axial movement of the middle drive sleeve 88 while allowing the drive sleeve to selectively rotate within the enlarged proximal end 86 of the outer sleeve 18 when the inner shaft 24 reaches its end of linear travel, as explained in more detail below.

The middle drive sleeve 88 includes a proximal end 98 and a distal end 100, each of which include ratchet teeth 102, 102'. The distal end 104 of the proximal drive ratchet ring 90 includes unidirectional ratchet teeth 106 that are configured to mate with the unidirectional ratchet teeth 102 of proximal end 98 of the middle sleeve 88. Similarly, the proximal end 108 of the distal drive ratchet ring 92 includes unidirectional ratchet teeth 110 that are configured to mate with the unidirectional ratchet teeth 102' of the distal end 100 of the middle sleeve 88.

The distal drive ratchet ring 92 is biased against the distal end 100 of the middle sleeve 88 so that the ratchet teeth are engaged and the proximal drive ratchet ring 90 is biased against the proximal end 98 of the middle sleeve 88 so that the ratchet teeth are engaged. In the illustrated embodiment, the distal drive ratchet ring 92 is biased by a spring 112, such as a wave spring, positioned between the distal end of the distal ratchet ring 92 and a shoulder 114 of the outer shaft 18. Similarly, the proximal drive ratchet ring 90 is biased against the proximal end of the middle sleeve 88 so that the ratchet teeth are engaged. In the illustrated embodiment, the proximal drive ratchet is biased by spring 116 positioned between the proximal end of the proximal ratchet ring 90 and a shoulder 118 of the handle 16.

Each of the middle sleeve 88 and the proximal and distal ratchet rings 90 and 92 includes stops or limiters that limit the linear movement of the inner shaft 24. In the illustrated embodiment, the stops are defined by pins 120 that pass through each of the respective middle sleeve 88, and proximal and distal ratchet rings 90 and 92. The pins 120 associated with the proximal and distal ratchet rings 90 and 92 also prevent the ratchet rings from rotating. In the illustrated embodiment, the pins 120 associated with ratchet rings 90 and 92 are inserted through the holes 122 in the enlarged proximal end portion 86 of the outer shaft 18. The holes 122 are elongated to allow the ratchet rings 90 and 92 to move linearly within the enlarged proximal end portion 86 of the outer shaft 18 while preventing the rings from rotating.

When the inner shaft 24 is rotated and the threaded section 80 of the shaft 24 is in the middle of its linear travel, the distal ratchet ring 92, the middle drive sleeve 88 and the proximal ratchet ring 90 are held together by the wave spring washers 112 and 166. The two ratchet rings 90 and 92 have opposed unidirectional teeth orientation such that each provides a counter-torque to the other one. Thus, when both ratchet rings 90 and 92 are engaged with the middle sleeve 88, the middle sleeve 88 is fixed and does not rotate. The middle sleeve 88 being fix, allows the inner shaft 24 to move linearly in the proximal and distal directions as the inner shaft 24 is rotated within the middle sleeve 88. As mentioned above the linear proximal and distal movement of the inner shaft 24 controls the angular motion of the tool 20.

Referring to FIG. 11, as the inner shaft 24 is turned clockwise, for instance, the inner shaft 24 moves distally until a distal shoulder 124 of the inner shaft 24 contacts the pin 120 associated with distal ratchet ring 92. When the shoulder 124 contacts the pin 120, the inner shaft 24 pushes against the pin 120 and moves the distal ratchet ring 92 so the ratchet teeth 110, 102' of the ring 92 and the middle sleeve 88 disengage, resulting in open the space between the ratchet teeth. Because the ratchet teeth 110 of the distal ring 92 are disengaged, the counter torque is no longer applied at the distal end of the middle sleeve 88 and the unidirectional teeth 104 of the proximal ring 90 will allow the teeth 102 of middle sleeve 88 to slip passed the teeth 104 of the proximal ring 90 as the sleeve is rotated clockwise, the middle sleeve 88 is now allowed to rotate with the inner shaft 24. Thus, the inner shaft 24 is allowed to free spin and the tool 20 at the end of the inner shaft 24 is allowed to spin even after the inner shaft 24 has reached is distal linear limit. When the inner shaft 24 is at is distal linear limit and then is turned counter clockwise, the ratchet teeth 104 of the proximal ring 90 prevent the middle sleeve 88 from rotating counter clockwise. With the middle sleeve 88 held stationary and the inner shaft 24 rotating counter clockwise, the inner shaft 24 move proximally and the shoulder 124 disengages the pins 120 associated with the distal ratchet ring 92. The spring 112 moves the ratchet ring 92 back into engagement with the middle sleeve 88, again applying a counter torque to the middle sleeve 88.

Similarly, as the inner shaft 24 is turned counter clockwise, the inner shaft 24 moves proximally until a proximal shoulder 126 of the inner shaft 24 contacts the pin 120 associated with the proximal ratchet ring 90. When the shoulder 126 contacts the pin 120, the inner shaft 24 pushes against the pin and moves the proximal ratchet ring 90 so the ratchet teeth 104, 102 of the ring 90 and the middle sleeve 88 disengage, resulting in open the space between the ratchet teeth 104, 102. Because the ratchet teeth of the proximal ring 90 are disengaged, the counter torque is no longer applied at the proximal end of the middle sleeve 88 and the unidirectional teeth 110 of the distal ring 92 are configured to allow the teeth 102' of the middle sleeve 88 to slip passed the teeth 110 of the distal ring 92 as the middle sleeve 88, the middle sleeve 88 is now allowed to rotate with the inner shaft 24. Thus, the inner shaft 24 is allowed to free spin and the tool 20 at the end of the inner shaft is allowed to spin even after the inner shaft 24 has reached its proximal linear limit. When the inner shaft 24 is at is proximal linear limit and then is turned clockwise, the ratchet teeth of the distal ring 92 prevent the sleeve 88 from rotating clockwise. With the sleeve 88 held stationary and the inner shaft 24 rotating clockwise, the inner shaft 24 moves distally and the shoulder 126 disengages from the pins 120 associated with the proximal ratchet ring 90. The spring 116 moves the ratchet ring 90 back into engagement with the middle sleeve 88, again applying a counter torque to the middle sleeve 88.

The free spin drive mechanism 84 allows to user to rotate the tool 20 freely at the end of travel whether it is in a straight position or in an angular position to allow for good endplate preparation by allowing that free end of travel spinning and therefore rendering the articulated tool instrument to be more effective.

Figure 12B:
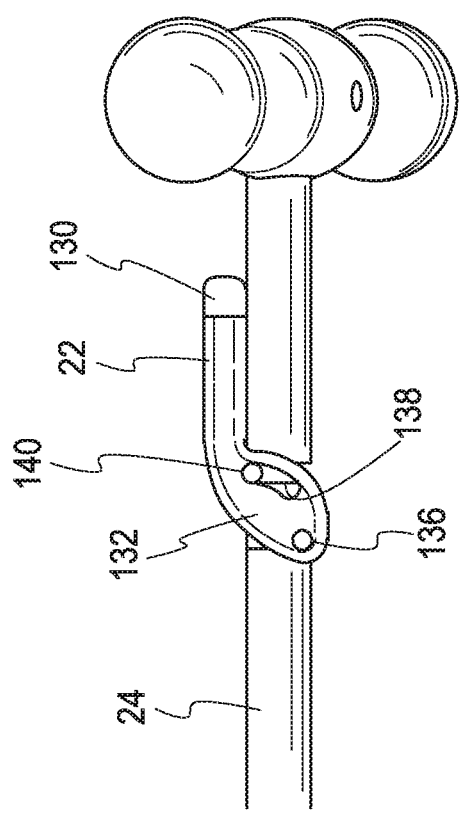
FIG. 12B is an enlarged side elevation view of the orientation tab and inner shaft.
Figure 12A:
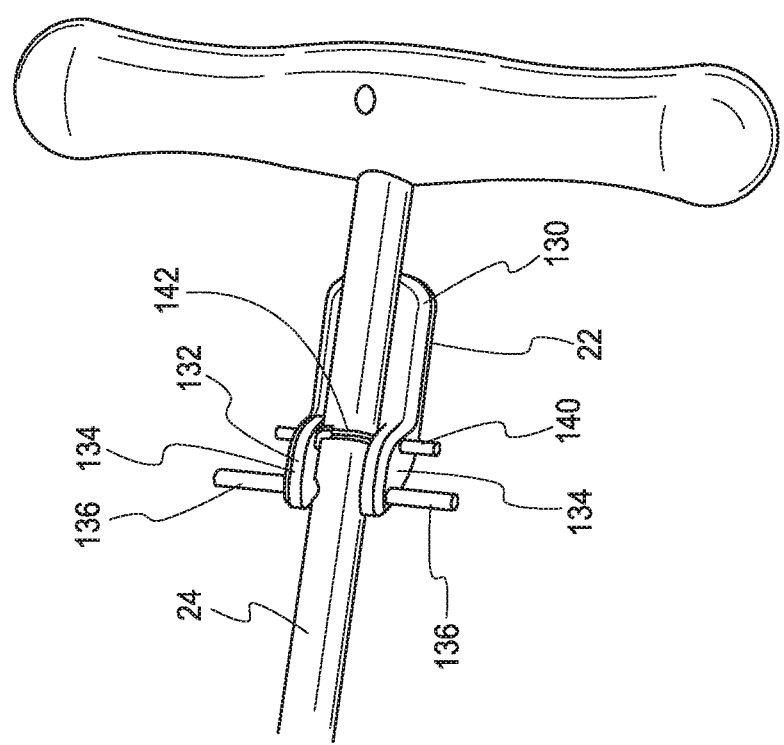
FIG. 12A is an enlarged perspective view of the orientation tab and inner shaft.

Turning to FIGS. 12A and 12B, these figures show an enlarged view of the orientation tab 22 in association with the inner shaft 24. The orientation tab 22 includes a tab 130 extending from a u-shaped body 132. The arms 134 of the u-shaped body 132 are positioned about the inner shaft 24. Pins 136 hingedly attach the body 132 of the orientation tab 22 to the handle (not shown). The arms 134 of the body 132 include a slot 138 which receives a pin 140. The inner shaft 24 includes a circumferential groove 142 which received the pin 140. As the inner shaft 24 moves proximally and distally, the pin 140 slides within the slot 138 and the orientation tab 24 pivots about pin 136. The position of the orientation tab 20 corresponds to the angular position of the tool 20 (FIGS. 1 and 2) to provide an indicator of the tool's position to the user.

Turning to FIGS. 13 and 14, there is shown another embodiment of an articulated instrument 210. The articulated instrument 210 includes a handle 212, an outer shaft 214, an inner shaft (drive shaft) 216 and a tool 218 at the distal end 220 of the instrument 210. The tool 218 may be any of the tools disclosed herein or any other suitable tool. In the illustrated embodiment, the tool 218 is a paddle shaver. The paddle shaver includes a paddle or blade like shape with two openings 222. The two openings 222 may be used to gather the tissue as it is being cut with the sharp edge 224, which may extend around partially or substantially around the periphery of the blade. As shown in FIGS. 14 and 16, the tool 218 may be moved into an angled configuration wherein the tool 218 is at an angle relative to the axis C of the outer and inner shafts 214 and 216. Furthermore, the tool 218 also is able to rotate about its axis D as it is moved into and from the angled configuration.

Referring to FIGS. 15-17, the tool may be connected to the distal end 226 of the inner shaft 216 by a u-joint 228. The u-join transfers rotational movement for the inner shaft 216 to the tool 218. The u-joint 228 includes a distal yoke 230 associated with the tool 218 and a proximal yoke 232 associated with the distal end 234 of the inner shaft 216. The u-joint further includes a spacer 236 (FIG. 17) that is connected to the distal and proximal yokes 230 and 232 by pins 238 and 240. The tool 218 is also connected to the distal end 242 of the outer shaft 214 by a hinged lever joint 244.

The hinge lever joint 244 includes a collar 246 attached to the tool 218 wherein the collar 246 allows the tool 218 to rotate therein. The hinged lever joint 244 also includes an arm 248 extending from the collar 246, wherein the arm 248 is hingedly attached to the outer shaft 214 by a pin 250.

As the inner shaft 216 is rotated, it moves distally relative to the outer shaft 214. This causes the collar 246 to pivot about the hinge connecting it the outer shaft 214, which in turn results in the tool 218 moving to an angled configuration relative to the shafts 214 and 218. Additionally, as the inner shaft 216 is rotated, the u-joint 228 translates rotational movement to the tool 218 so that the tool rotates. Thus, the joints 228 and 244 allow the tool 218 to move into an angled position and be simultaneously rotated. FIGS. 16 and 17 show the tool angulated at about 60° to the axis C of the inner and outer shafts 214, 216. The dashed line 252 seen in FIGS. 15 and 17 identify the theoretical position of an implant in the disc space and are there to show that the angular motion of tool 218 sweeps across the whole area of the implant position that would be in a disc therefore allowing for substantially or complete removal of disc tissue in that area before the implant is inserted and deployed.

FIGS. 20A and 20B and FIGS. 21A and 21B illustrate the drive mechanism 254 and the movement of the tool 218 as the inner shaft 216 is rotated and moved linearly. The drive mechanism 254 includes a drive sleeve 256 which is held in handle 212 by pins 258. The sleeve 256 includes an internal thread 257 which mates with an external thread 259 on inner shaft 216. When the inner shaft 216 is rotated, the linear travel of the inner shaft 216 is limited by stops within the drive sleeve 256. In the illustrated embodiment, pins 258 serve as stops or limiters. For instance, in FIG. 20B, when the inner shaft 216 is rotated in the counter clockwise direction, the shaft moves proximally, thereby moving the tool 218 into the straight configuration, as shown in FIG. 20A. The inner shaft 216 moves proximally until the shoulder 260 of the shaft contact pins 258, which prevents further proximal movement. Similarly, in FIG. 21B, when the shaft 216 is rotated in the clockwise direction, the shaft 216 moves distally, thereby moving the tool 218 into an angled configuration, as shown in FIG. 21A. The inner shaft 216 moves distally until shoulder 262 of the shaft 216 contacts the other side of pins 258, which prevents further distal movement.

The action generated by the inner shaft's 216 forward/distal motion translates in the angulation of the tool 218 from a straight position in FIG. 20A to the angular position in FIG. 21A. So not only the rotation translates in a forward motion via drive mechanism 254 but the rotation also allows the tool to rotate as it swings in its angular motion about lever joint 244 via the u-joint 228.

The instrument, optionally, may include a limited torque driver assembly associated with the inner shaft 216. The limited torque driver assembly may be any suitable limited torque driver assembly that allows the development of a torque motion in a controlled limited fashion.

Turning to FIGS. 18 and 19, these figures illustrate alternative embodiments of articulated instruments. Referring to FIG. 18, the articulated instrument 264 includes an ergonomic handle 266 that has a visual indication of the orientation of tool angulation. For example, the handle 266 may include a rib 268 to indicate the orientation of the tool 270 angulation. In addition, markings 272 may be on the outer shaft to provide a depth gage and, optionally, a visual indication of tool angulation. The markings 272 allow the physician to understand the positioning depth and, optionally, orientation of the tool 270. FIG. 19 illustrates another embodiment of the articulated instrument 274 without a proximal handle attached to the proximal end 276 of the inner shaft 278. The proximal end 276 of the inner shaft 278 has a quick connection element 280, which may have the illustrated square configuration, which sometimes is referred to as a Square Quick-Connect. The quick connection element 280 may be used to connected a variety of handle and/or torque drivers.

Figure 22:
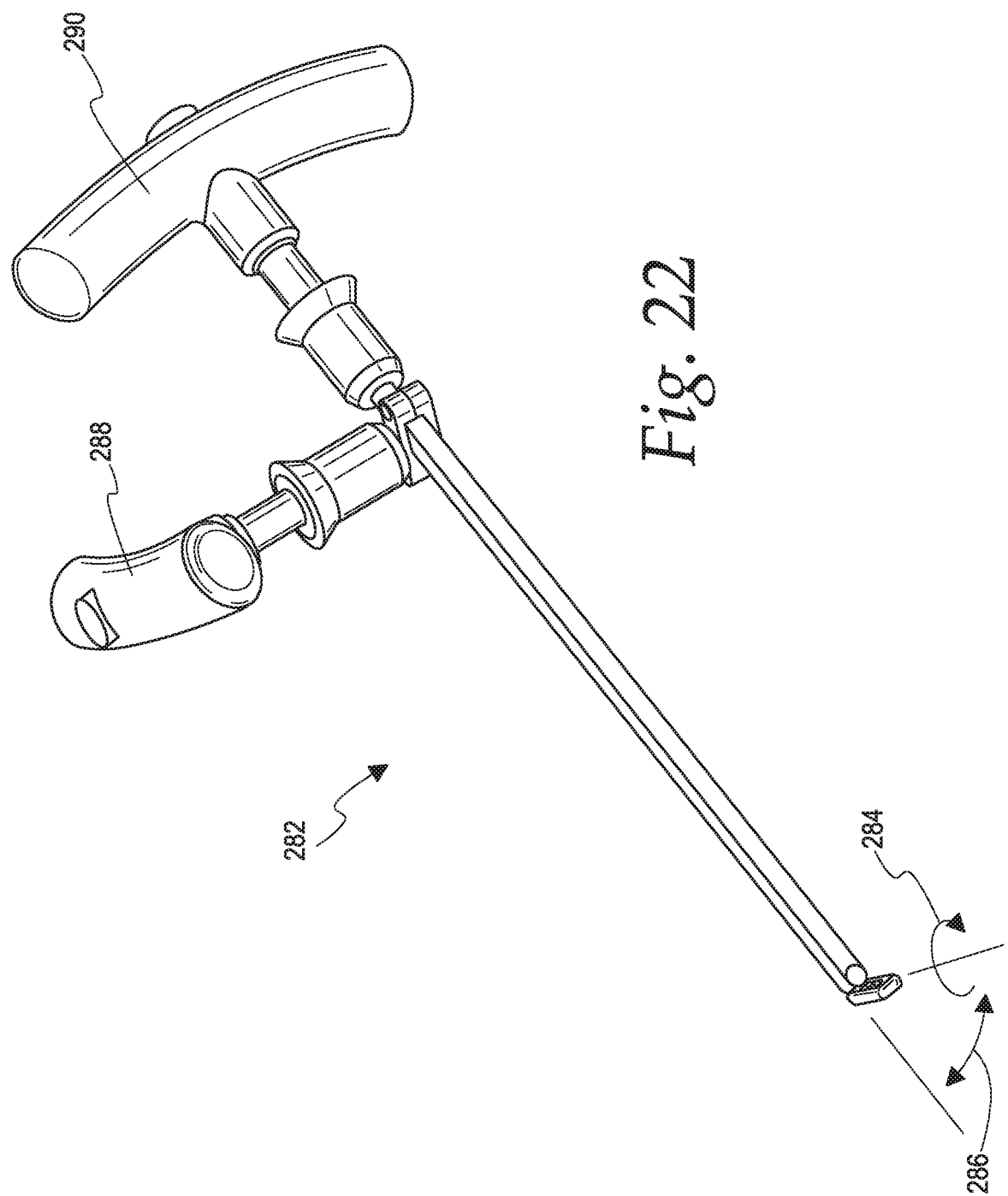
FIG. 22 is a perspective view of another embodiment of the articulated instrument.

FIG. 22 shows another embodiment of an articulated instrument 282, which may be an articulated shaver where the two motions, tool rotation 284 and angular motion 286 are decoupled and can each be separately activated with handle 288 controlling tool rotation 284 and handle 290 controlling angular motion 286. During use, the rotation and angular motion can occur independently or the user and employ a two handed operation to obtain simultaneous motions.

Figure 23:
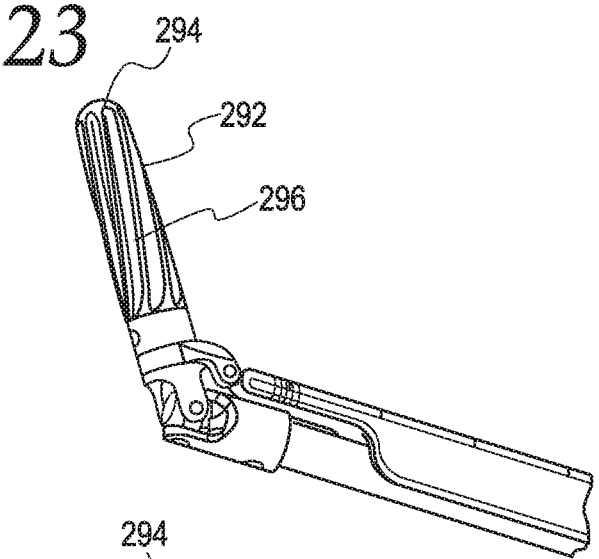
FIG. 23 is a perspective view of a burr distal tip mounted an articulated instrument of the present disclosure.
Figure 24:
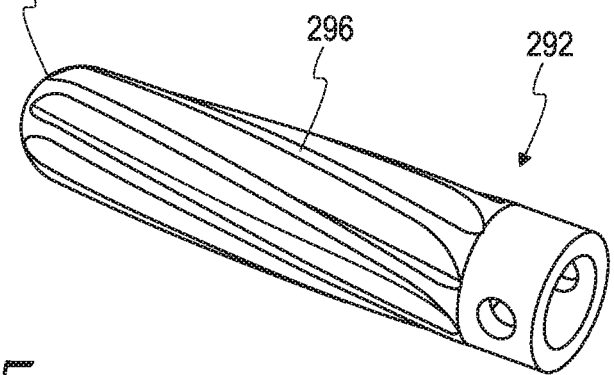
FIG. 24 is a perspective view of the burr of FIG. 23.

Turning to FIGS. 23 and 24, an articulated rotating burr 292 is shown mounted on the distal end of an articulating instrument, such as any of the above described instruments. The rotating burr 292 functions to the provide the user with the ability to grind away harder material such as osteophytes, bone spurs or other endplate irregularities in order to provide a very clean and even surface before deployment of an implant interbody fusion device. The burr 292 has a cylindrical or conical shape with a blunt distal tip 294 with either set of parallel straight or helical cutting edges 296 extending along the length of a cylindrical or conical body.

Figure 25:
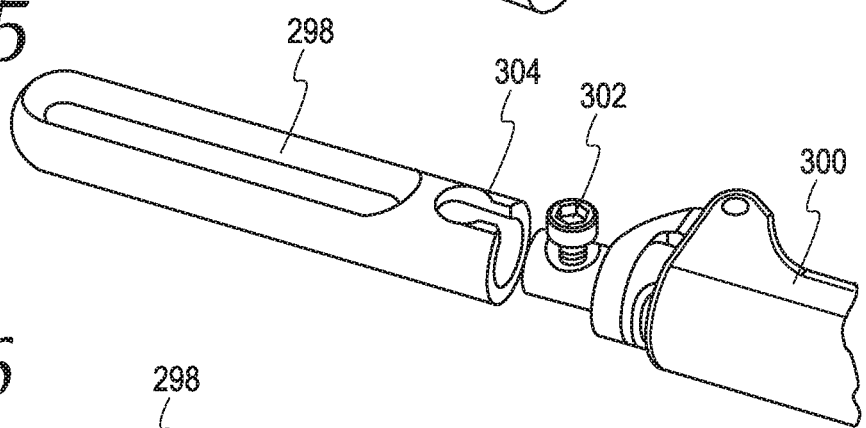
FIG. 25 is a perspective view of one embodiment of a detachable tip.
Figure 26:
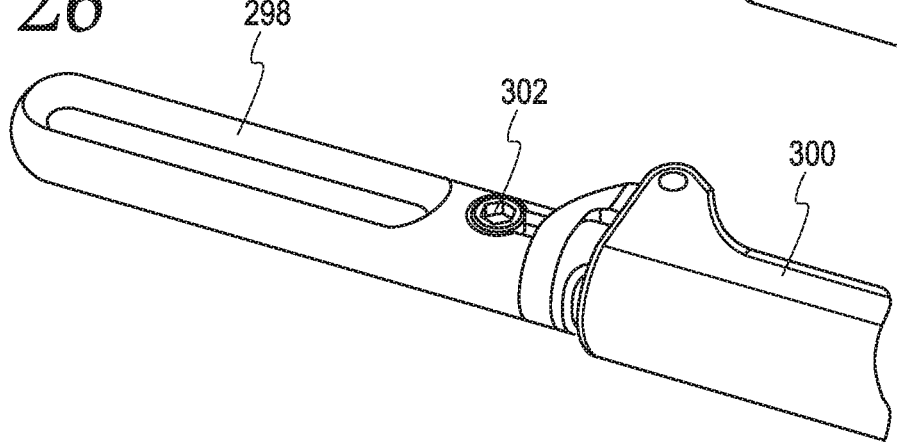
FIG. 26 is a perspective of the detachable tip of FIG. 25, shown attached to an articulated instrument of the present disclosure.

FIGS. 25 and 26 illustrate a removable tool 298 that can be removed from the instrument 300. The tool 298 may be any suitable disruption tool, such as a burr, blade, shaver tips, scraper or rasp, that can be removable from the instrument. The tool 298 may be attached by side set screw 302 that can be loosened to remove to replace the tool and re-tighten to attach a tool. The tool 298 may include a slot 304 that accepts the screw 302 when the tool 298 is attached to the instrument 300. The removable system provides a quick disconnect that allows the user to choose between a variety of tools and tool sizes. The removable tool could be connected to the instrument in other manners, such as a snap ring or quick disconnect type of mechanism.

Turning now to FIGS. 27-37, these figures illustrates another embodiment of an articulated instrument 310. The articulated instrument 310 includes a handle 312, a lever 314, a cannula or shafts 316 and a tool 318. The tool 318 may be any tool described herein, such as a scraper, blade, rasp, etc. The split cannula 316 may be made of two half shafts, a lower half shaft 320 and an upper half shaft 322. The lower half shaft 320 and the upper half shaft 322 are connected by pins 324 and are slidable relative to one another. In the illustrated embodiment the upper half shaft 322 includes elongated slots 326 which the pins 324 are passed through and which allow the half shafts to slide relative to one another.

Figure 31:
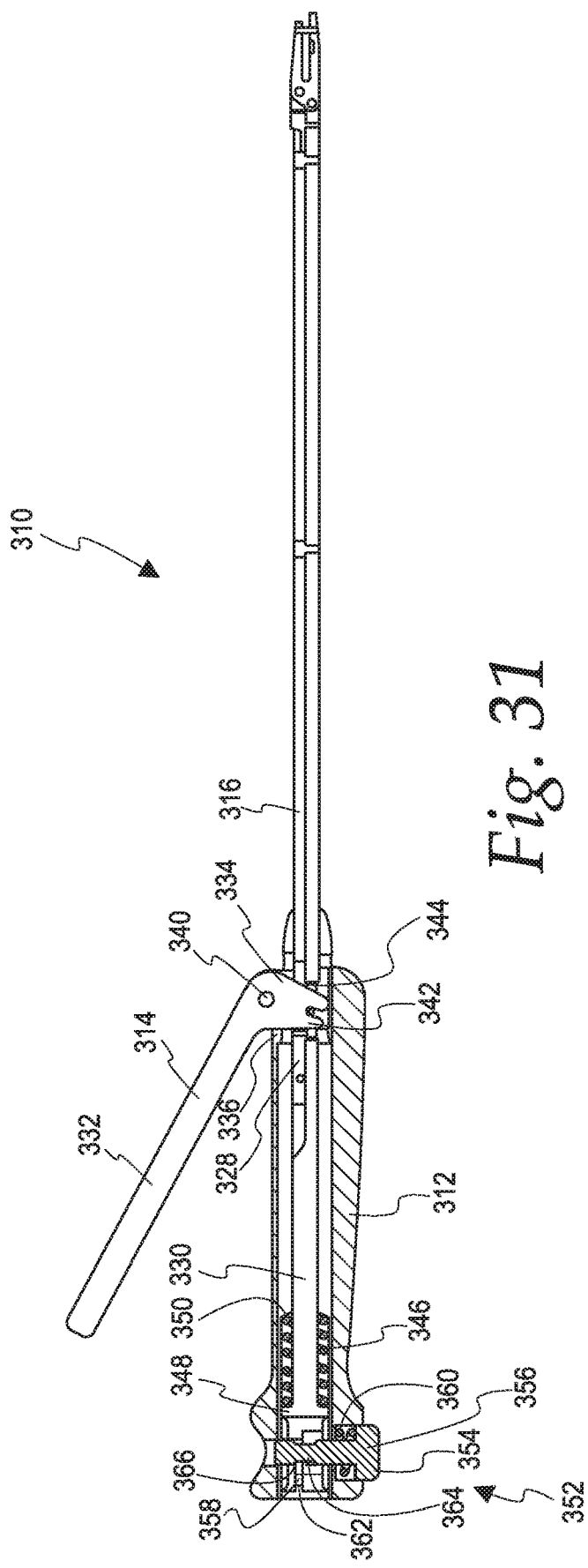
FIG. 31 is cross-sectional view of the instrument of FIG. 27.

Referring to FIGS. 31-33, the proximal end portion 328 of the upper half shaft 322 and the proximal end portion 330 of the lower half shaft 320 are located in the handle 312. The lever 314 associated with the handle 312 is used to slide the lower half shaft 320 distally relative to the upper half shaft 322. The lever 314 includes an arm 332 and a base 334. The base 334 extends through an opening 336 in the handle 312 and through an opening 338 in the upper half shaft 322. The base 334 is attached to the handle 312 by pin 340. The base 334 of the lever 314 includes a u-shaped member 342 that engages slots 344 in the lower half shaft 320. The lever 314 pivots about pin 340 so that when the arm 332 of the lever 314 is moved toward the handle 312, the u-shaped member 342 moves distally. Movement of the u-shaped member 342 distally results in moving the lower half shaft 320 distally.

The lever 314 is biased so that the arm 332 of the lever 314 is spaced from the handle 312. In one embodiment, the handle 312 is biased by a spring 346. In the illustrated embodiment, a spring 346 is positioned about the proximal end portion 330 of the lower half shaft 320. The spring 346 is also positioned between a head 348 at the proximal end 330 of the lower half shaft 320 and a wall 350 within the handled 312. Referring to FIGS. 32 and 33, in FIG. 32, in the initial position, the lever 314 is biased by the spring 346 so that the arm 332 is positioned away from the handle 312. When the arm 332 is moved toward the handle 312, the lever 314 pivots about pin 340 and the u-shaped member 342 moves the lower half shaft 320 relative to the upper half shaft 322. Additionally, when the lower half shaft 320 is moved distally, the head 348 at the proximal end 330 of the lower half shaft 320 moves distally and compresses the spring 346. When pressure is relieved from the lever 314, the spring 346 biases the lower half shaft 320 to move proximally back to its initial position, thereby moving the lever 314 back to its initial position.

Figure 34:
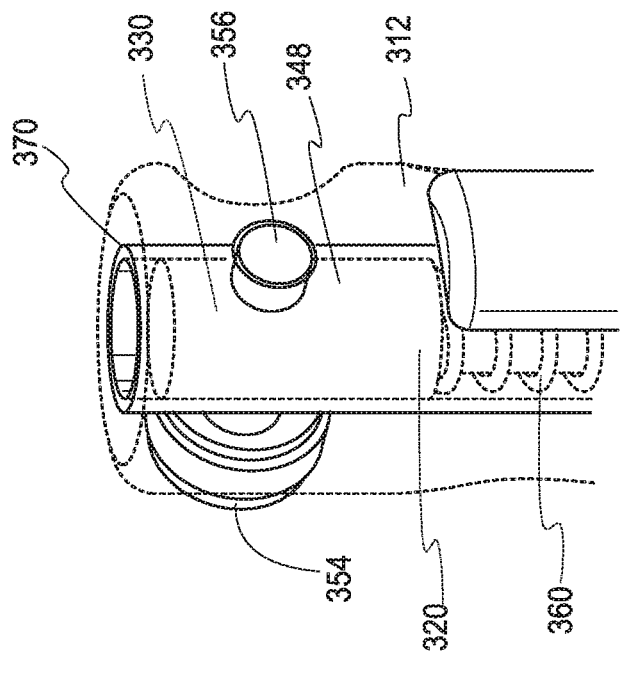
FIGS. 34 and 35 are perspective views of the proximal end of the handle of the instrument of FIG. 27.
Figure 35:
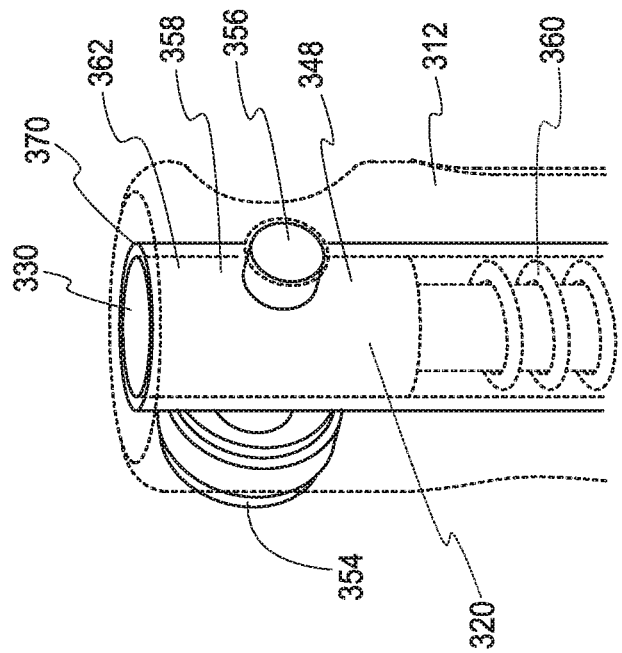

Referring to FIGS. 33-35, optionally, the instrument may include a releasable lock that locks the instrument in the second position. In the illustrated embodiment, the lock 352 is a spring release lock that includes a button 354 and a post 356 extending therefrom and into the handle 312. The post 356 also extends through a slot 358 in the head 348 of the lower half shaft 320. The lock 352 is biased downward by a spring 360 that is positioned between the button 354 and the handle 312. When the lower half shaft 320 is moved distally by moving the arm 332 of the lever 314 toward the handle 312, a shoulder 362 in the slot 358 of the head 348 of the lower half shaft 320 engages a groove 364 in the post 356 of the lock. The downward force on the button 354 provided by spring 360 holds an upper wall 366 of the groove 364 of the post 356 against the shoulder 362 in the slot 358 of the head 348 of the lower half shaft 320. When the button 354 is pushed upward, the upper wall 366 of the groove 364 disengages the shoulder 362 and the lower half shaft 320 moves distally.

Referring to FIGS. 34, 35, 39 and 40, the handle 312 may include a visual indicator indicating the position of the lower half shaft and the position of the tool. In the illustrated embodiment, the proximal end of the handle 312 includes an opening or bore 370 in which the proximal end 330 of the lower half shaft 320 is located. When the proximal end 330 of the lower half shaft 320 is flush with the outer surface of the handle 312 surrounding the bore 370, the instrument is in its initial position. When the proximal end 330 of the lower half shaft 320 is below the outer surface of the handle 312, the lower half shaft 320 has been moved distally which in turn indicates that the tool has been moved into a second position.

Figure 37:
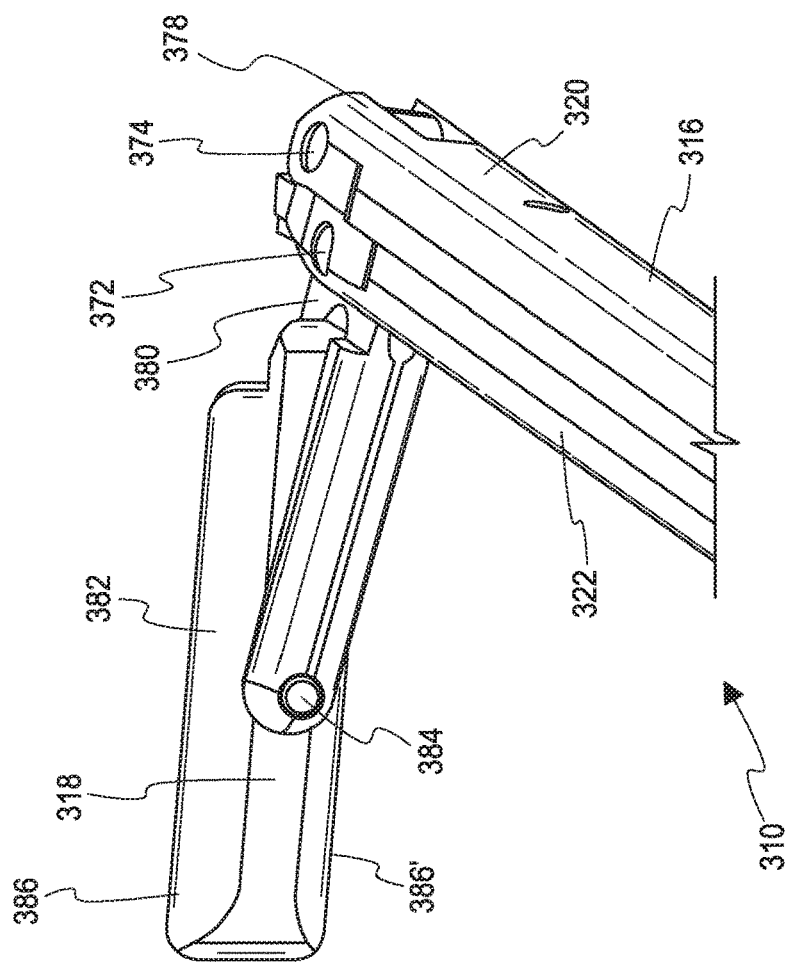
FIGS. 36 and 37 are perspective views of one embodiment of a tool that may be used with the instrument of FIG. 27.
Figure 36:
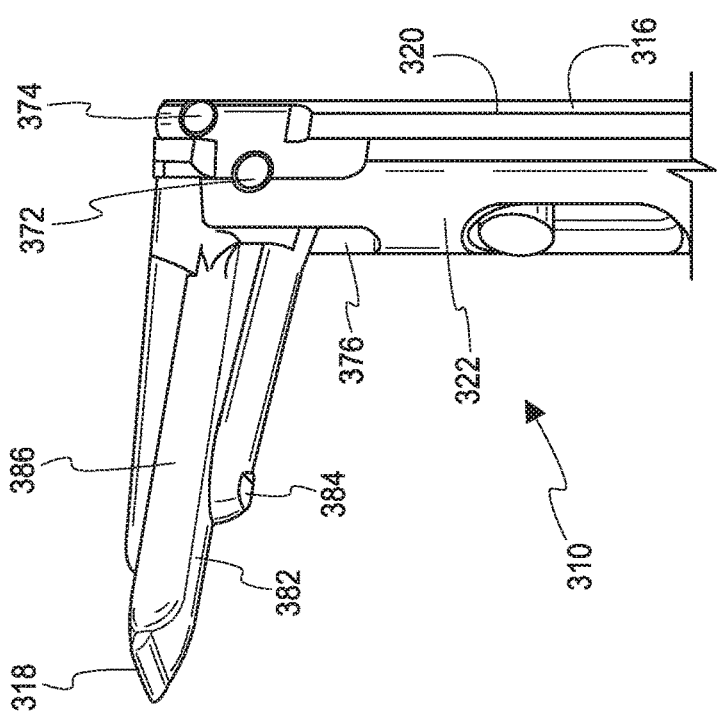

Referring to FIGS. 36 and 37, a tool 318, such as a scrapping blade, is located at the distal end of the instrument 310. The tool 318 is hingedly attached to the upper half shaft 322 by pin 372 and attached to the lower half shaft 320 by pin 374. In the illustrated embodiment, the distal end of the upper half shaft 322 includes a u-shaped connection element 376 and the distal end of the lower half shaft 320 includes a u-shaped connection element 378. The tool includes a u-shaped bracket 380 which includes a portion that is located within the u-shaped connection element 376 of the upper half shaft 322 and a portion located within the u-shaped connection element 378 of the lower half shaft 320. The portions are hingedly connected by pins 372 and 374. A blade 382 is positioned between the u-shaped bracket 380 of the tool 380 and hingedly connect to the bracket 380 by pin 384. The blade 382 that can pivot about pin 384 so the double scraping edge of the blade 386 and 386' are maintained in contact with the endplate for optimize scraping (one at the time based on the bias of the user toward the superior or inferior endplate). As shown in these two figures, the blade 382 can fully rotate about the pivot 384 but it could also be made to have a limited motion about pivot 384 with some stop posts to prevent full rotation of the blade 382 (not shown).

When the tool 318 is to be moved to 90° relative to the axis of half shafts 320, 322, the lever 314 is moved toward the handle 312 which moves the lower half shaft 320 distally relative to the upper half shaft 322. When the lower half shaft 322 moves distally, the tool 318 pivots around pin 372 associated with the upper half shaft 322 and pin 374 associated with the lower half shaft 320, thereby moving the tool 318 into a portion that is 90° relative the axis of the half shafts.

FIG. 38 illustrates another embodiment of an articulated instrument 388 which includes a u-shaped flipping lock 390 which is pivoted about the distal end of the handle 312. When the lever 314 is moved adjacent to the handle 312, the lock 390 is pivoted to cover the lever 314 and hold it in position. The lock 390 can then be pivot to uncover and release the lever 314. FIGS. 39 and 40, show the lock 390 in combination with a visual indicated as discussed above.

FIGS. 41 and 42 show another embodiment of an articulated instrument 400. In this embodiment, the upper and lower half shafts 402 and 404 interact with each other in the same manner as described above. Similarly, lever 406 is associated with handle 408 and the lower half shaft 404 in the same manner as described above. In this embodiment, the handle 408 includes windows or holes 410 which allows for less material and a lighter handle.

FIG. 43-45 illustrate embodiment of tools 412 and 414 that may be used with any of the instruments shown in FIGS. 27-42, 49, 51 and 53. In these embodiments, the tools 412 may include different components that are assembled together to provide movement and adjustability. The tools 412 and 414 include a bracket 416, 416' and a working piece 418, 418' that may pivot relative to the bracket 416, 416'. The proximal end 420, 420' of the bracket may be mounted or attached to the distal end of an instrument 422 (FIG. 45). In the illustrated embodiment, the bracket includes a pair of arms 424, 424' that may be mounted to the upper and lower half shafts 426, 428 of the instrument 422. Referring to FIG. 45, the upper and lower half shafts 426, 428 are connected by a pin 430 that extends through elongated opening 432 in the upper half shaft 426 and connects to lower half shaft 428. As described above, the lower half shaft 428 moves linearly relative to the lower half shaft 426.

Figure 46:
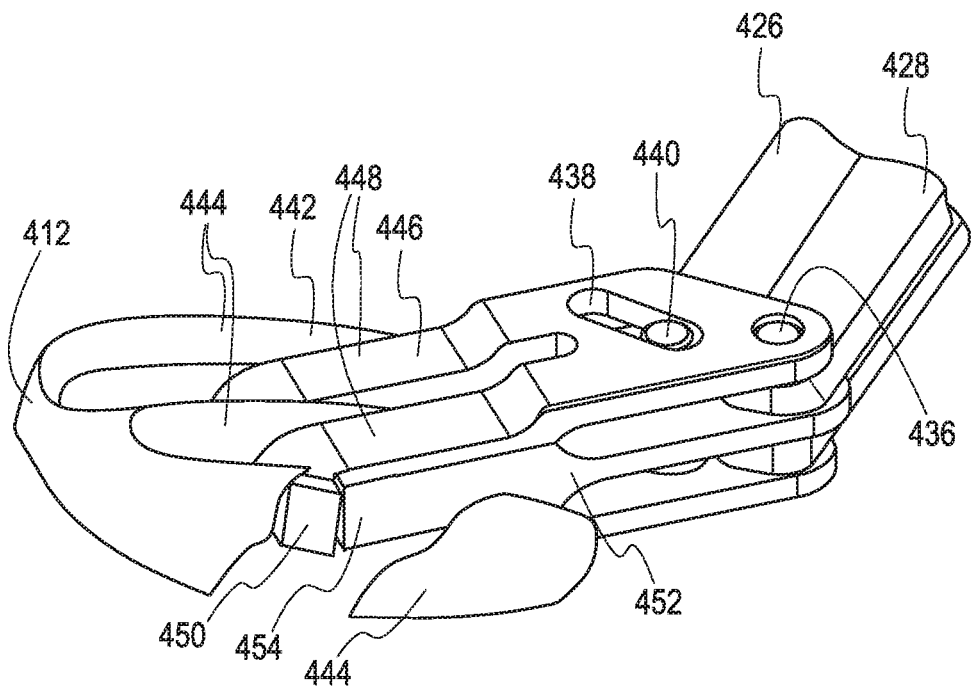
FIG. 46 is a perspective cut-away view of the tool of FIG. 43 which shows a motion limiter.
Figure 47:
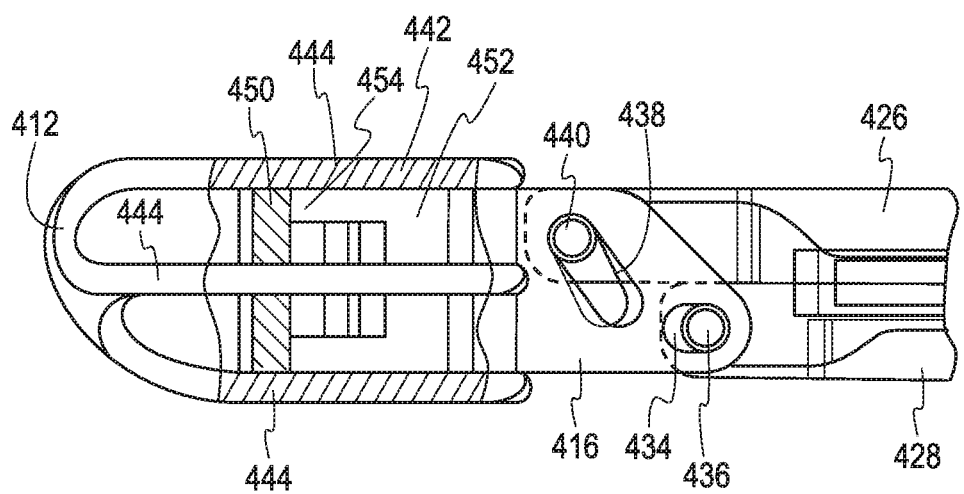
FIG. 47 is a top plan partially cut-way view, showing the tool in a straight configuration.
Figure 48:
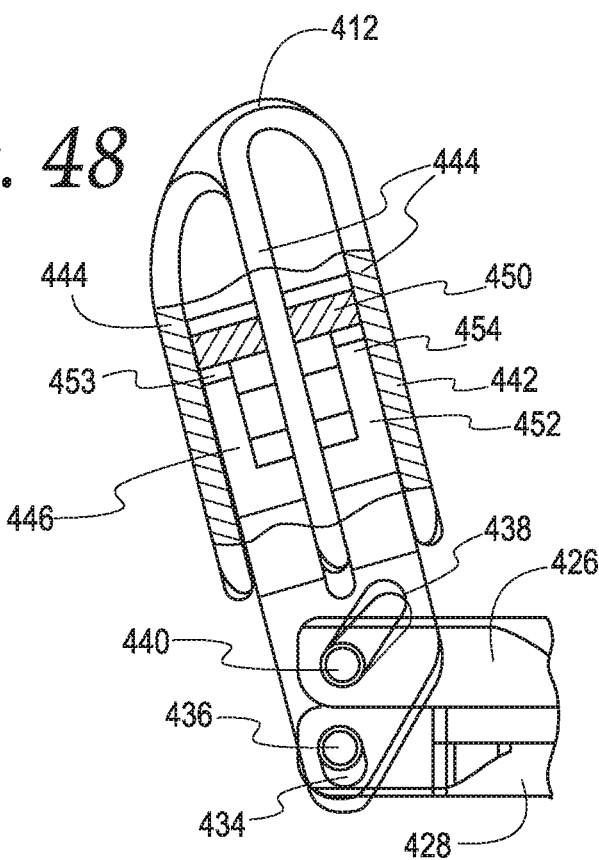
FIG. 48 is a top plan partially cut-way view, showing the blade in an angled configuration.
Figure 65:
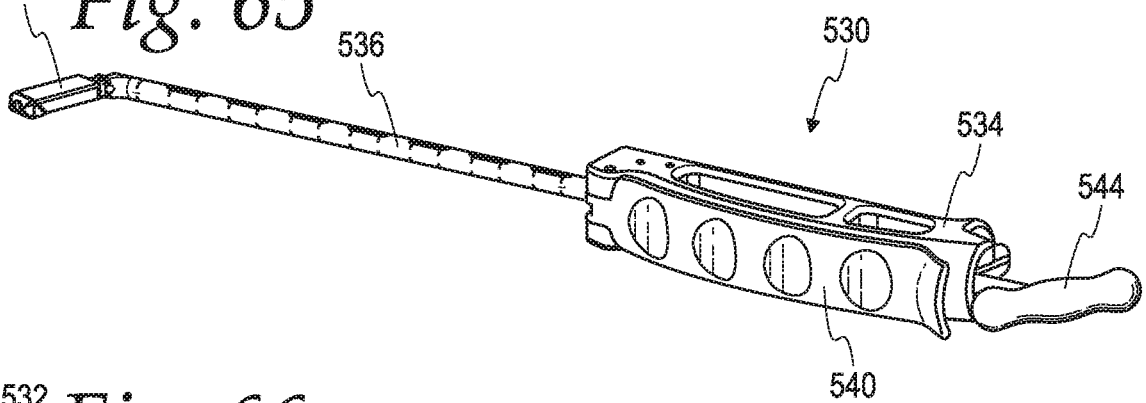
FIG. 65 is a perspective view of one embodiment of an articulated instrument having a distraction tip.

Referring to FIGS. 45-48, each of the arms 424, 424' of the brackets 416, 416' includes lower opening 434, 434' which may be mounted to the lower half shaft 428 with a pin 436. Each of the arms 424, 424' of the brackets 416, 416' includes an upper opening 438, 438' which may be mounted to the lower half shaft 428 with a pin 440. The upper openings 438, 438' are elongated so as to allow the pin 440 to slide within the opening as the tool is moved into the angled configuration. In these embodiments, the arms 424, 424' are placed on either side of the lower half shaft 428 and upper half shaft 426 and pins 436 and 440 extends through arms to attached them to the half shafts. In FIG. 47, the tool 412 is in the straight configuration and the pin 440 is located at the upper end of the elongated opening 438. Referring to FIG. 48, when the lower half shaft 428 is moved distally and the tool 412 is angled relative to the shafts 426, 428, as described above, the pin 440 slides within the opening 438 to the other end of the elongated opening.

In FIGS. 43, and 46-48 the working piece 418 is a blade, and in FIGS. 44 and 45, the working piece 418' is a rasp with sharp teeth. The teeth may be on both the working piece and the bracket. The proximal ends 442, 442' of each working piece 418, 418' include three arms 444, 444' for attachment to the distal end 446, 446' of its respective bracket 416, 416', which includes two arms 448, 448'. Each working piece 418, 418' is attached to its respective bracket 416, 416' by meshing the three arms 444, 444' of the working piece 418, 418' with the two arm 448, 448' of the bracket 416, 416'. A pin 450, 450 is then inserted through the three arms 444, 444' of the working piece 418, 418'. The working piece may pivot about the pin during use. In one embodiment, the working piece has the ability to pivot about + or −30° relative to the bracket. This assists in the working piece being more compliant to the surface of the endplate having an optimize contact over the full length of the blade or the rasp.

Referring to FIGS. 45 and 46, the tool 412, 412' may include a limiter 452, 452' that limits the movement of the working piece 418, 418'. The limiter includes a distal end 454, 454' that contacts the working piece 418, 418' or pin 450, 450' to limit the range of pivoting of the working piece about pin 450, 450'. Referring to FIG. 45, the limiter 452' includes a proximal end 456' that has an upper opening 458' and a lower opening 460', which are similar in size and shape to openings 434' and 438' of the bracket '416. The limiter 452' is placed between the arms 424' of the bracket 416' and the proximal end of the limiter 452' is placed between arms of the upper and lower half shafts 426, 428. The limiter 452' is attached to the upper and lower half shafts 426, 428 by pins 436 and 440. Referring to FIG. 48, the limiter 452 is slightly off-set during the articulation leaving a gap 453 where the pin 450 has the necessary opening to pivot as the distal end of 454 of the limiter 452 is not in contact with a flat the pin 450 as also. This opening gap allows the scraper or rasp working piece to pivot about the axis of pin 450 until edge contact between the distal end of the limiter 452 and the flat of pin 450. Referring to FIG. 47, the gap (453 of FIG. 48) is closed in the straight configuration. This action can be accomplished by adjusting the ramp angle of the upper elongated opening of the limiter (e.g. 458' of FIG. 45) to be slightly different than the ramp angle of the elongated opening 438 (FIG. 47) of the bracket 416.

FIG. 49 illustrates another embodiment of an articulated instrument 470. In this embodiment, the handle 472 includes a rotating knob 474 to articulate the tool 476 instead of a lever mechanism as previously described. The benefit of the rotating knob 474 is that the user would be able to control the angle of the tool 476. For example, the knob 474 may have a multiple intermediary positions as shown by the slots 478 that could be for position at 0 and every 15° thereafter all the way to 90° for instance. Other increments could be used as well.

FIG. 51 illustrates another embodiment of an articulated instrument 480 that includes a pistol like grip device 482. The grip 482 may include a first handle 484 and a second handle 486 that a pivoted relative to one another. The first handle 484 may be connected to the upper half shaft 488 and the second handle 486 may be connected to the lower half shaft 490. When the handles 484 and 486 are moved toward each other, the lower half shaft 490 moves distally relative to the upper half shaft 488. The handles may be biased apart by a spring 492.

FIG. 52*a* and FIG. 18*b* are enlarged views of tools 494 and 496 that are of a one-piece construction and include different rasp patterns. Tool 494 includes rows of teeth having an angled configuration 53 that would provide rasping action (tissue/cartilage removal) in one direction (in this illustrated orientation, it would be from a posterior to an anterior direction). Tool 496 includes teeth that are more universal and pyramid shaped like allowing tissue removal in all directions. FIG. 53 illustrates the one-piece construction tool 494 attached to an instrument 498, which may be used during a discectomy for the final preparation of the endplate to smooth out the surface in order to clear out any irregularities, extra tissue, small osteophytes and cartilage defects or imperfection that could prevent the insertion of an interbody implant device. The instrument is an articulated instrument, such as those described about with respect to FIGS. 27-45

The disclosed instrumentation may be used during the discectomy part of a greater procedure for fusion or disc replacement by the placement of an interbody implant device. The disclosed instrumentation may also be used to remove tissue from other parts of the body. In one embodiment, the disclosed instruments may be used in disc preparation procedures where an incision would be made in the annulus, followed by the removal of a cut-out window in the annulus, which may be about 10 mm wide, and the height of the disc at that particular level.

Referring to FIGS. 54-58, once that window 501 is completed, any of the articulated instruments described herein may be used to penetrate the nucleus 503 in a straight fashion in line with the access axis. Once that instrument is inserted, it is then rotated (the entire instrument is rotated so the tip blade cuts out the tissue without lateral or angular motion) about the axis to debulk the nucleus tissue, a standard tissue grasper such as a pituitary tool may be used to remove some of the tissue bulk before the next step is taken.

Figure 54:
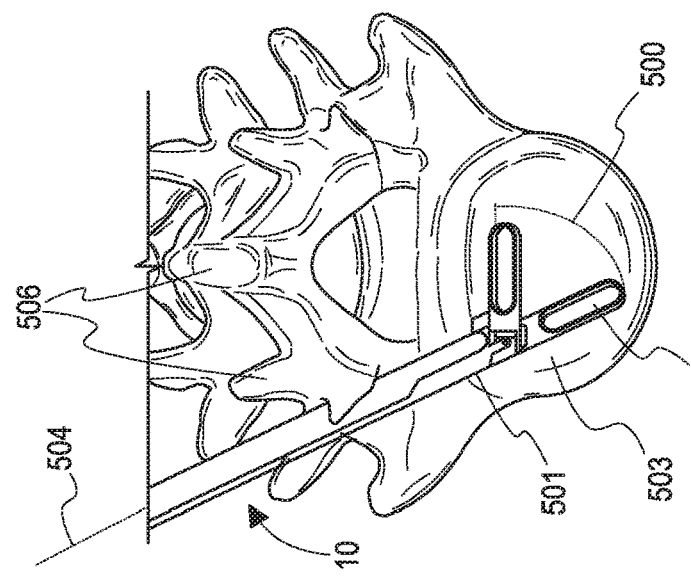
FIG. 54 is a perspective view of an articulated instrument within a disc space.

During this next step, instrument 10 (FIG. 1) may be used to create a larger space to accommodate the implantation of an interbody implant, such as a fusion device or a disc replacement device. By turning the knob 24 of the instrument 10, the tool 20, which may be a shaver, will rotate as well as swept across the area 500 in the disc space as shown in FIG. 54 and in a manner as previously disclosed and this action can be repeated several times with the use of pituitary tools in between for tissue removal until the physician feels that the majority or most of the nucleus tissue is removed. Instrument 10 has the ability to clean-out a large area away from the axis of insertion 504 without any motion of the instrument itself, unlike a standard shaver that needs to be sway back and forth in order to reach the same surfaced area and in some cases, could not be able to because of interference with body structure 506 or with the supporting access devices such as retractor or spreader (not shown). In addition, in the case of a MIS (Minimally Invasive Surgery) where a tube access system is used, the ability to sway a discectomy instrument may not be available or desired.

Figure 55:
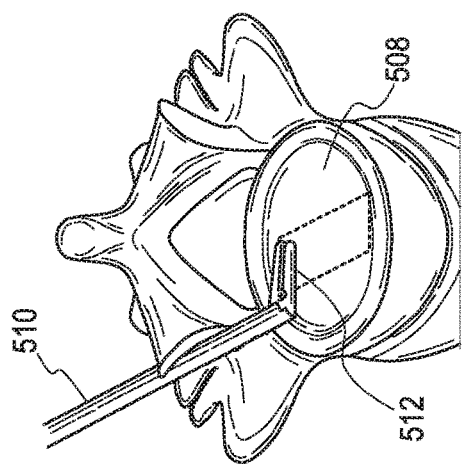
FIGS. 55 and 56 are perspective views of an articulated instrument within a disc space.
Figure 56:
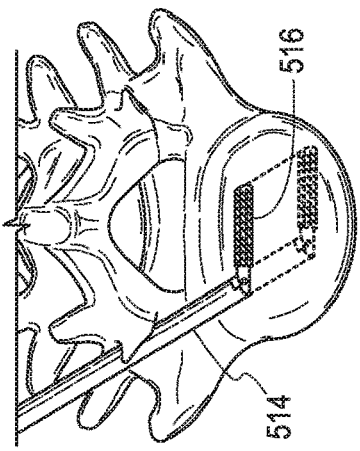

Following the debulking of the nucleus tissue, the next step is the preparation of the end plate 508. The articulated instrument 510 is used to remove further tissue that is still attached to the endplate in the same general area of where the nucleus was removed as it is shown in FIGS. 55 and 56. Again the instrument is inserted in the straight configuration (FIG. 55) along axis 504 and then the tool 512 is angled into an angled configuration (FIG. 56). The instrument 510 can then can be moved back and forth (FIG. 56) in a motion from posterior to anterior and until a sufficient amount of tissue is removed. The loose tissue can be aspirated or removed with pituitary tools as well.

Figure 57:
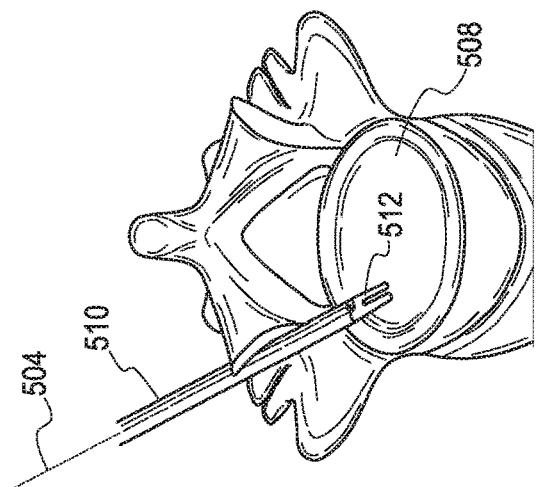
FIGS. 57 and 58 are perspective views of an articulated instrument within a disc space.
Figure 58:
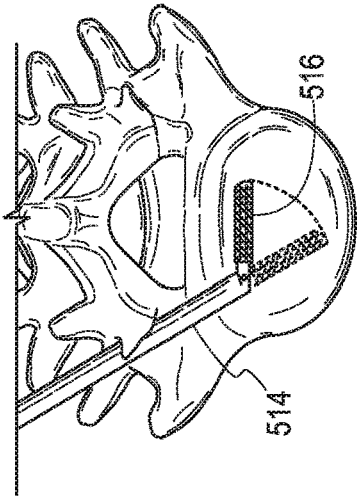

Referring to FIGS. 57 and 58, the surface preparation of the endplate can be completed by using an articulated instrument 514 that includes an articulated rasp 516. As shown in these figures, the instrument may be inserted and used in the same manner as shown in FIGS. 55 and 56.

Upon completion of the disc preparation, the space can be sized and the appropriate interbody implant, such as a fusion device or disc replacement implant can be inserted and the procedure completed.

FIGS. 59-61 illustrate the use of articulated instrument 310 of FIGS. 27-37. The instrument 310 is inserted into the disc space 520 in a straight configuration and then the tool 318, such as a pivoting curette or blade, is moved into an angle configuration relative to shaft 316. The shaft 316 is rotated so that the blade 382 of the tool 318 contacts the endplates 522. As shown in the figures, the blade 382 may pivot relative to the bracket 380. The shaft is moved back and forth to shave tissue from the endplates 522.

FIGS. 62-63 illustrate the use of articulated instrument 498 of FIG. 53. The instrument 498 is inserted into the disc space 520 in a straight configuration and then the tool 494, such as a rasp, is moved into an angle configuration relative to shaft. The shaft is rotated so that the tool 494 contacts the endplates 522. As shown in the figures, the shaft is moved back and forth to shave tissue from the endplates 522.

Figure 66:
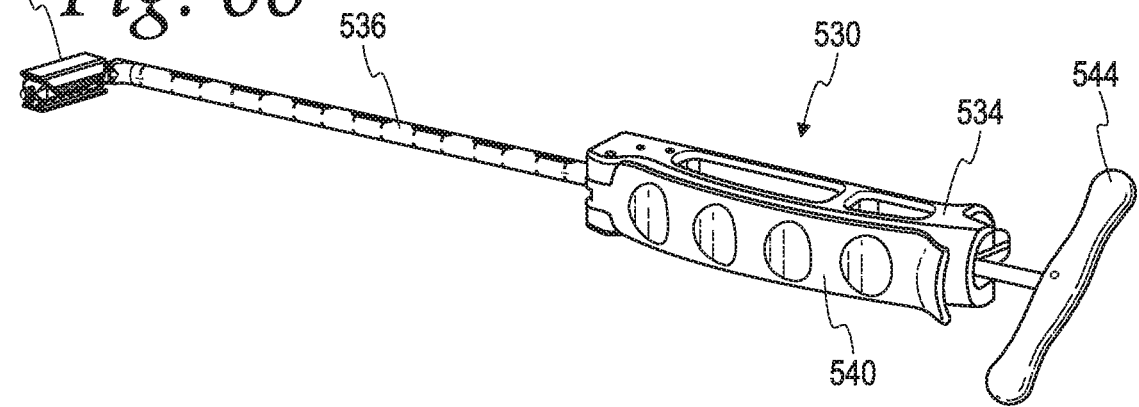
FIG. 66 is a perspective view of the articulated instrument of FIG. 65 shown in the expanded configuration.
Figure 68:
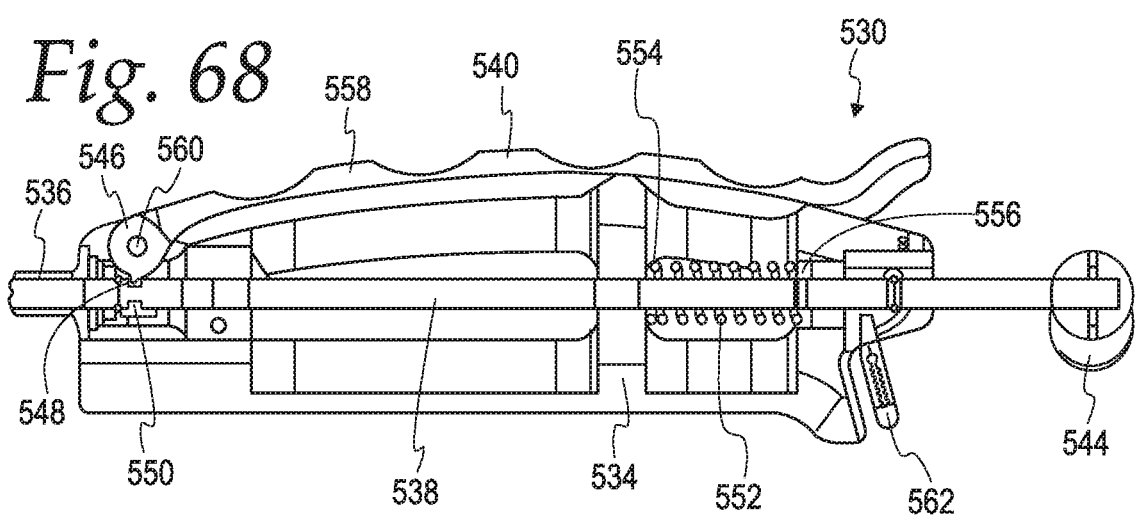
FIG. 68 is an enlarged cross-sectional view of the handle of the articulated instrument of FIG. 65.
Figure 69:
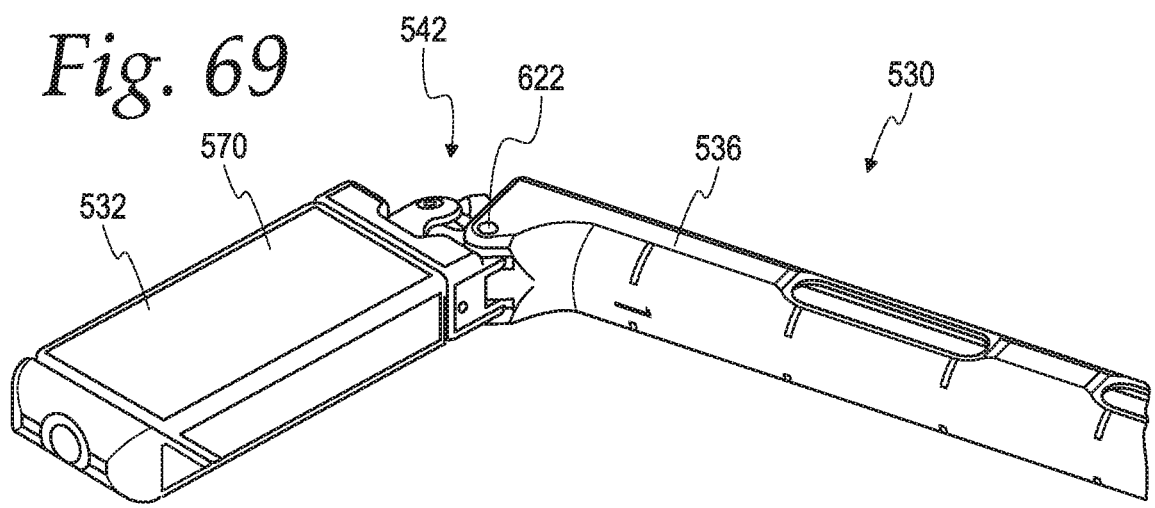
FIG. 69 is a perspective view of the distal end of the articulated instrument of FIG. 65 shown in the compact configuration.
Figure 70:
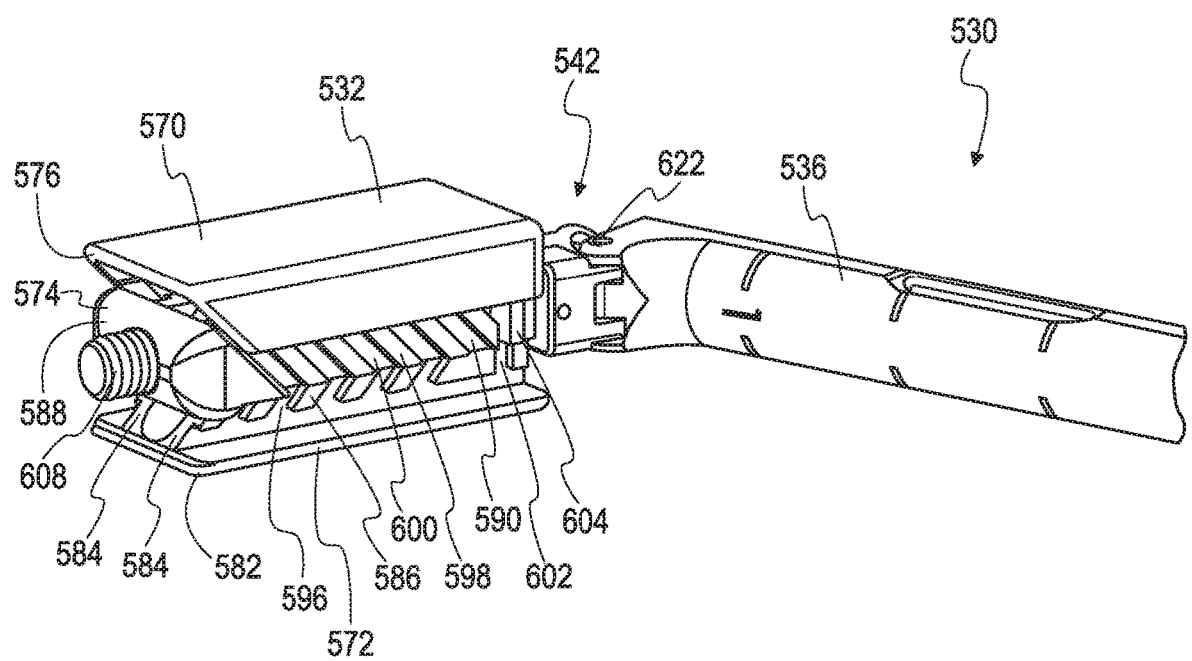
FIG. 70 is a perspective view of the distal end of the articulated instrument of FIG. 65 shown in an expanded configuration.

FIGS. 65-71 illustrate another embodiment of an articulated instrument 530 wherein the tool is a distraction tool 532 that may be used to move tissue apart, such as to distract adjacent vertebral bodies. The instrument 530 includes a handle 534, an outer shaft 536, an inner shaft 538 (drive shaft) and the distraction tool 532. The instrument 530 uses a hybrid combination of a lever 540 to control the linear movement of the inner shaft 538 and a u-joint 542 to translate rotational movement to the tool 532. The distraction tool 532 may be angled up to 60°, relative to the axis of the shafts 536, 538, using a single U-Joint (such as that shown in FIGS. 15-17) or up to 75° using a double U-Joint (such as that shown in FIGS. 4-6). As explained in more detail below, the rotational movement transferred to the distraction tool 532 may be used to expand the tool, as shown in FIGS. 66 and 70.

Figure 67:
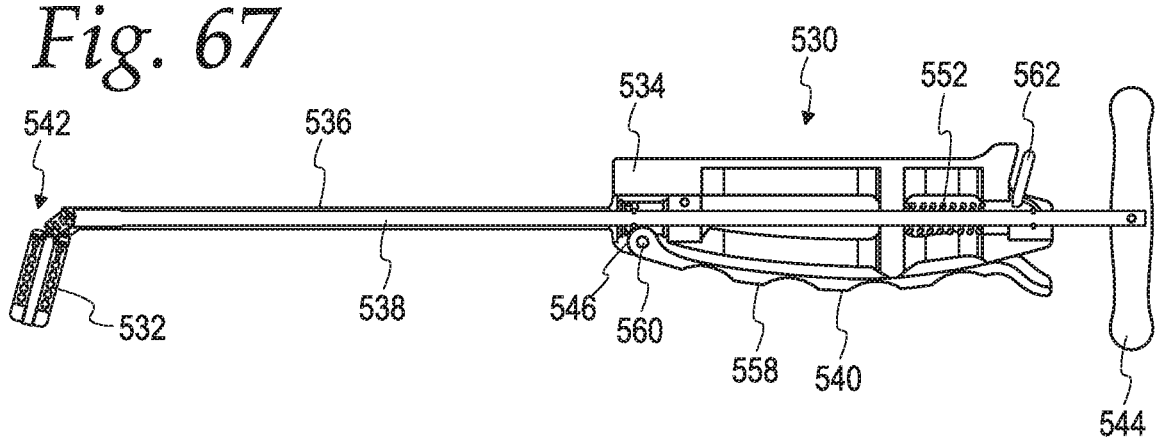
FIG. 67 is a cross-sectional view of the articulated instrument of FIG. 65.

FIG. 67 illustrates a full cross-section of the entire instrument 530 and FIG. 68 is an enlarged cross-sectional view of the handle 534. The inner shaft 538 extends through the handle 534 and the outer shaft 536. A knob 544 for turning the inner shaft 538 is located at the proximal end of the shaft 538. The handle 534 includes lever 540, which has similar structures and operates in the same manner as lever 314 shown in FIG. 31. The lever 540 includes a body 546 that has an extension 548, such as one or more arms, that mates with a groove 550 in the inner shaft 538 (FIG. 68). The engagement between the extension 548 and groove 550 allows the shaft 538 to rotate within the handle. The inner shaft 538 is biased to the proximal position by a spring 552, which is located between a wall 554 of the handle 534 and a shoulder 556 extending radially outward from the shaft 538.

The operation of the lever 540 is very similar to that shown in FIGS. 31-33. The lever 540 is biased so that the arm 558 of the lever 540 is spaced from the handle 534 (the instrument is not shown in this position). When the arm 558 is moved toward the handle 534, the lever 540 pivots about pin 560 and the extension 548 of the handle body 546 moves the inner shaft 538 distally relative to the outer shaft 536. Additionally, when the inner shaft 538 is moved distally, the shoulder 556 at the proximal end of the inner shaft 538 moves distally and compresses the spring 552. When pressure is relieved from the lever 540, the spring 552 biases the inner shaft 538 to move proximally back to its initial position, thereby moving the lever 540 back to its initial position.

The inner shaft 538 is rotated by knob 544 to provide rotating action to the distal distraction tool 532, while the lever 540 provides the articulation of the tool. An indicator tab 562 may be used to indicate the orientation of the tool 532 in a similar fashion as previously discussed with respect to indicator tab 22 and as shown in FIGS. 12A and 12B.

Figure 71:
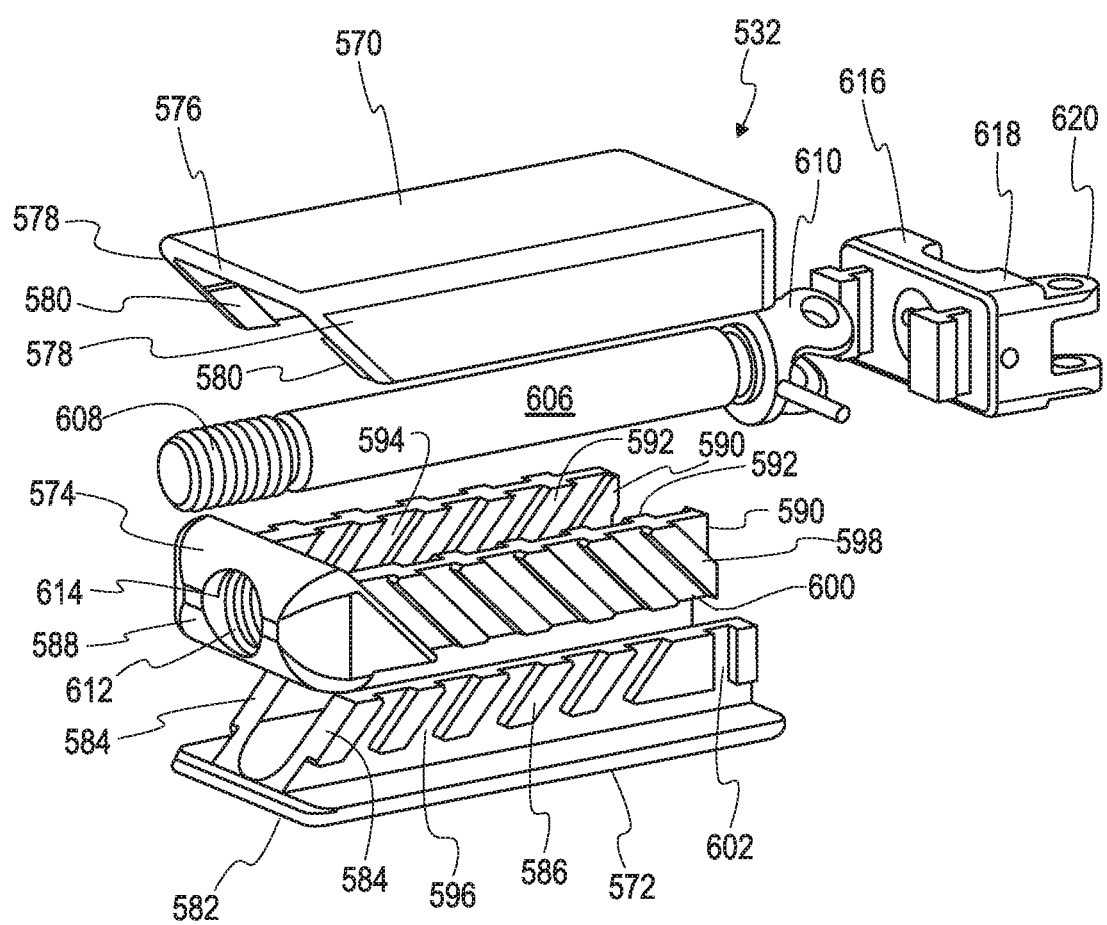
FIG. 71 is an exploded view of the distraction tip of FIG. 65.

FIG. 71 illustrates an exploded view of the distraction tool 532. The tool includes an upper member 570, a lower member 572 and a middle member 574. The upper member 570 is generally u-shaped and includes an upper plate or surface 576 for contacting tissue. In the illustrated embodiment, the upper surface 576 is shown a flat but in other embodiment, the upper surface 576 may be curved or textured. The upper member 570 includes a pair of opposed side walls 578 extending downward form the upper surface 576. The inner surface of the opposed side walls 578 include a plurality of angled ramps 580. In one embodiment the ramps 580 are angled at 45°.

The lower member 572 includes a lower plate or surface 582 which a pair of opposed arms 584 extending upward form the lower surface 582. The opposed arms 584 are spaced inward of the edges of the lower surface 582. Additionally, the outer surface of the opposed arms 584 include a plurality of ramps 586 that are angled in the opposite direction from the ramps 580 of the upper member 570. In one embodiment the ramps 586 are angled at 45° in the opposite direction from the ramps 580 of the upper member 570.

The middle member 574 includes a front wall 588 and a pair of opposed arms 590 extending from the front wall. The inner surface of the opposed arms 590 include a plurality of ramps 592 that are angled in the opposite direction from the ramps 586 of the lower member 572. The lower member 572 and middle member 574 are configured to mate such that the arms 584 of the lower member 572 are placed inside of the arms 590 of the middle member 574 and the ramps 586 of the lower member 572 are positioned in the space 594 between or adjacent to the ramps 592 of the inner surface of the middle member 574. Similarly, the ramps 592 are positioned in the space 596 between the ramps 586 of the lower member.

The outer surface of the arms 590 of the middle member 574 include ramps 598 that are angled in the opposite direction from the ramps 580 of the upper member 570. The upper member 570 and middle member 574 are configured to mate such that the arms 578 of the upper member 570 are placed outside of the arms 590 of the middle member 574 and the ramps 580 of the upper member 570 are positioned in the space 600 between the ramps 598 of the outer surface of the middle member 574. Furthermore, the upper member 270 and lower member 274 each include a slot 602 (not shown in the upper member) that receives a rail 604 (FIG. 70) vertically positioned within the slots.

The distraction tool 532 includes an actuation member 606, which is includes external threads 608 on distal end and a yoke 610 on the proximal end. The yoke 610 attaches to or is a part of the u-joint 542, such as a u-joint or double u-joint as described above. The external threads 608 on the distal end of the actuation member 606 engage internal threads 612 of a bore 614 through the front wall 588 of the middle member 574. The distraction tool 532 also includes a hinged lever 616 that is attached to the outer shaft 536. The hinged lever 616 is similar to hinged lever 34 shown in FIGS. 4-6. In the illustrate embodiment, the hinged lever 616 includes a collar 618 having a pair of arms 620 extending therefrom. The collar 618 is located about actuation member 606 and the arms 620 are hingedly attached to the outer shaft 736 by a pin 622 (FIGS. 69 and 70).

In use, the distraction tool 532 is inserted into a disc space in the straight configuration. The lever 540 is moved toward the handle 534 to move the distraction tool 532 into an angled configuration. The knob 544 is used to rotate inner shaft 538 wherein the rotating motion is translated via the u-joint or double U-joint 542 to the actuation member 606 of the distraction tool. The engagement of the threaded distal end 608 of the actuation member 606 with the internal threads 612 of the middle member 574 pulls the middle member 574 proximally relative to the upper and lower member 570, 572. As the middle member 574 moves from a distal location, as shown in FIG. 69, to a more proximal location, shown on FIG. 70, the ramps 592, 598 of the middle member 574 act upon the corresponding ramps 580, 586 on the upper member 570 and the lower member 572 to spread apart the upper and lower members. The upper member and lower member 570, 572 move in a vertical direction as they are guided by rail 604 with the corresponding engagement on each of the upper member and lower member. After the distraction tool 532 has been expanded to a selected height, the inner shaft 538 is rotated in the other direction to move the middle member 574 distally, which in turn moves the upper and lower member 570, 572 back toward the unexpanded configuration shown in FIG. 69.

It is understood that the foregoing merely illustrates the principles of the various embodiments of the systems, device and methods disclosed herein. Various modifications and alterations to the described embodiments will be apparent to those skilled in the art in view of the teachings herein.

The invention claimed is:

1. An articulated disc preparation instrument, comprising:
a handle having a proximal end and a distal end;
an outer shaft extending from the distal end of the handle;
an inner shaft extending within the outer shaft; and
a disruption tool hingedly attached to the distal end of the inner shaft and hingedly attached to the distal end of the outer shaft, wherein when the inner shaft is rotated, the disruption tool rotates with the inner shaft, wherein when the inner shaft is moved linearly relative to the outer shaft the disruption tool moves between a first straight configuration wherein an axis of the disruption tool is parallel to an axis of the outer shaft and a second angled configuration wherein the disruption tool is at an angle relative to the outer shaft, wherein rotation of the inner shaft when the disruption tool is in between the first straight configuration and the second angled configuration causes both rotation of the disruption tool and a change in the angular articulation of the disruption tool.

2. The articulated instrument of claim 1 wherein the disruption tool is connected to the distal end of the inner shaft by a u-joint.

3. The articulated instrument of claim 1 wherein the disruption tool is connected to the distal end of the inner shaft by a double u-joint.

4. The articulated instrument of claim 3 wherein the disruption tool is connected to the distal end of the outer shaft by a hinged lever.

5. The articulated instrument of claim 4 wherein the hinged lever includes a collar, wherein the collar is configured to allow the disruption tool to rotate therein.

6. The articulated instrument of claim 1 further including a drive mechanism that moves the inner shaft linearly when the inner shaft is rotated.

7. The articulated instrument of claim 6 wherein the drive mechanism comprises a sleeve having internal threads, and wherein the inner shaft extends through the sleeve and includes external threads that are mated with the internal threads of the sleeve.

8. The articulated instrument of claim 7 wherein the drive mechanism comprises a free spin drive mechanism that allows the drive shaft to continuously rotate.

9. The articulated instrument of claim 8 wherein the free spin drive mechanism includes first and second counter torque ratchet rings, wherein the first counter torque ratchet ring is moveably engaged with a distal end of the sleeve and the second counter torque ratchet ring is moveably engaged with the proximal end of the sleeve.

10. The articulated instrument of claim 9 wherein the sleeve rotates with the inner shaft when either one of the first and second ratchet rings are disengaged from the ends of the sleeve.

11. The articulated instrument of claim 10 wherein the inner shaft moves the first ratchet ring out of engagement with the distal end of the sleeve when the inner shaft reaches a distal linear travel limit.

12. The articulated instrument of claim 11 wherein the inner shaft moves the second ratchet ring out of engagement with the proximal end of the sleeve when the inner shaft reaches a proximal linear travel limit.

13. The articulated instrument of claim 12 wherein the first and second ratchet rings are biased into engagement with the sleeve.

14. The articulated instrument of claim 6 wherein the drive mechanism is located in the handle.

15. The articulated instrument of claim 1 wherein the disruption tool comprises one or more of a shaver, scraper, burr, blade, and rasp.

16. The articulated instrument of claim 1 wherein the disruption tool comprises a paddle shaver having a paddle or blade like shape with two openings configured to gather tissue as it is being cut.

17. The articulated instrument of claim 1 further including an orientation indicator, which indicates a position of the disruption tool relative to the axis of the outer shaft.

18. The articulated instrument of claim 1 wherein the disruption tool is configured to move through a range of angles up to 120°.

19. The articulated instrument of claim 1, wherein the disruption tool freely rotates without linear translation of the inner shaft when the disruption tool is in the first straight configuration.

20. The articulated instrument of claim 1, wherein the disruption tool freely rotates without linear translation of the inner shaft when the disruption tool is in the second angled configuration.

* * * * *